(12) United States Patent
Ye

(10) Patent No.: US 9,040,713 B2
(45) Date of Patent: May 26, 2015

(54) METHODS OF MANAGING BLOOD SUGAR LEVELS AND COMPOSITIONS RELATED THERETO

(75) Inventor: Keqiang Ye, Lilburn, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 0 days.

(21) Appl. No.: 13/818,391

(22) PCT Filed: Sep. 27, 2011

(86) PCT No.: PCT/US2011/053396
§ 371 (c)(1),
(2), (4) Date: Feb. 26, 2013

(87) PCT Pub. No.: WO2012/047628
PCT Pub. Date: Apr. 12, 2012

(65) Prior Publication Data
US 2013/0158082 A1 Jun. 20, 2013

Related U.S. Application Data

(60) Provisional application No. 61/386,823, filed on Sep. 27, 2010, provisional application No. 61/478,561, filed on Apr. 25, 2011.

(51) Int. Cl.
| | |
|---|---|
| *A61K 31/428* | (2006.01) |
| *A61K 31/122* | (2006.01) |
| *A61K 31/4439* | (2006.01) |
| *C07C 69/65* | (2006.01) |
| *C07C 225/30* | (2006.01) |
| *C07C 321/22* | (2006.01) |
| *C07D 277/84* | (2006.01) |
| *C07D 307/92* | (2006.01) |
| *C07D 417/12* | (2006.01) |

(52) U.S. Cl.
CPC ........... *A61K 31/122* (2013.01); *A61K 31/4439* (2013.01); *A61K 31/428* (2013.01); *C07C 69/65* (2013.01); *C07C 225/30* (2013.01); *C07C 321/22* (2013.01); *C07D 277/84* (2013.01); *C07D 307/92* (2013.01); *C07D 417/12* (2013.01)

(58) Field of Classification Search
CPC ............ A61K 31/4439; A61K 31/428; A61K 31/122; C07D 417/12; C07D 277/84
See application file for complete search history.

(56) References Cited

U.S. PATENT DOCUMENTS 6,262,096 B1    7/2001   Kim et al.
2004/0198716 A1  10/2004  Arad

FOREIGN PATENT DOCUMENTS

| JP | 06340526 | | 12/1994 |
|---|---|---|---|
| JP | 11021239 | A * | 1/1999 |
| WO | 2008008033 | | 1/2008 |
| WO | WO 2008008033 | A1 * | 1/2008 |
| WO | 2009122432 | | 8/2009 |

OTHER PUBLICATIONS

Huang et al. Bioorg. Med. Chem. 1998, 6, 2261-2269.*
Hussain et al. Diabetes Research and Clinical Practice 2007, 76, 317-326.*
Bruno et al. Expert Opinion Emerging Drugs, (2005), 10(4), pp. 747-771.*
Colagiuri et al. American Journal of Public Health, Sep. 2006, vol. 96, No. 9, pp. 1562-1569.*
MayoClinic, Type 1 diabetes—Prevention, obtained from http://www.mayoclinic.org/diseases-conditions/type-1-diabetes/basics/prevention/con-20019573 on Jun. 2, 2014.*
Park, Diabetes Research and Clinical Practice 66S (2004), S33-S35.*
Curtis et al. The Journal of the American Board of Family Practice, vol. 18, pp. 37-43, (2005).*
CAS Registry No. 883799-76-6, which entered STN on May 11, 2006.*
Curtis et al., Preventing Type 2 Diabetes Mellitus, JABFP Jan.-Feb. 2005 vol. 18 No. 1.
Park, Diabetes Research and Clinical Practice, vol. 66, Supplement, Dec. 2004, pp. S33-S35.
Colagiuri et al., The Answer to Diabetes Prevention: Science, Surgery, Service Delivery, or Social Policy? American Journal of Public Health | Sep. 2006, vol. 96, No. 9.
Bruno et al., Emerging drugs for diabetic nephropathy, Expert Opin. Emerging Drugs (2005) 10 (4):747-771.
Hussain et al., Prevention of type 2 diabetes: A review, Diabetes Research and Clinical Practice vol. 76, Issue 3, Jun. 2007, pp. 317-326.
Huang et al. Synthesis and antiplatelet, antiinflammatory, and antiallergic activities of substituted 3-chloro-5,8-dimethoxy-1,4-naphthoquinone and related compounds. Bioorg Med Chem. 1998;6(12):2261-2269.
Paull et al., Some Substituted Naphthazarins as Potential Anticancer Agents, Journal of Medicinal Chemistry, 1976, vol. 19, No. 2 p. 337-338.

(Continued)

*Primary Examiner* — Joseph Kosack
*Assistant Examiner* — Matthew Coughlin
(74) *Attorney, Agent, or Firm* — Emory Patent Group

(57) ABSTRACT

The disclosure relates to methods of managing blood sugar levels and compositions related thereto. In certain embodiments, the disclosure relates to methods of treating or preventing diabetes, insulin resistance, or hyperglycemia comprising administering to a subject diagnosed with, at risk of or exhibiting symptoms of diabetes, insulin resistance, or hyperglycemia a pharmaceutical composition comprising a compound comprising formula I.

11 Claims, 18 Drawing Sheets

(56) References Cited

OTHER PUBLICATIONS

Karlos et al., Activities of naphthoquinones against *Aedes aegypti* (Linnaeus, 1762) (Diptera: Culicidae), vector of dengue and *Biomphalaria glabrata* (Say, 1818), intermediate host of *Schistosoma mansoni*, Acta Tropica 111 (2009) 44-50.

He et al. Identification of a molecular activator for insulin receptor with potent anti-diabetic effects, J Biol Chem. 2011, 286(43):37379-88.

He et al., Identification of a molecular activator for insulin receptor with potent anti-diabetic effects. J Biol Chem., 2012;287(16): 13050.

Gastaldelli et al., The Effect of Rosiglitazone on the Liver: Decreased Gluconeogenesis in Patients with Type 2 Diabetes 2006 The Journal of Clinical Endocrinology & Metabolism 91(3):806-812.

Gastaldelli et al., Thiazolidinediones improve beta-cell function in type 2 diabetic patients, 2007, Am J Physiol Endocrinol Metab. 292(3):E871-83.

Zhang et al., Discovery of a Small Molecule Insulin Mimetic with Antidiabetic Activity in Mice, 1999, Science, vol. 284 No. 5416 pp. 974-977.

Lin et al., Identification of novel orally available small molecule insulin mimetics, 2007, J. Pharmacol. Exp. Ther. 323, 579-585.

\* cited by examiner

METHODS OF MANAGING BLOOD SUGAR LEVELS AND COMPOSITIONS RELATED THERETO

CROSS REFERENCE TO RELATED APPLICATIONS

This application claims priority to U.S. provisional application 61/386,823 filed Sep. 27, 2010 and U.S. provisional application 61/478,561 filed Apr. 25, 2011 both hereby incorporated by reference in their entirety.

ACKNOWLEDGEMENTS

This invention was made with government support under Grants CA 127119 awarded by the National Institutes of Health. The government has certain rights in the invention.

BACKGROUND

Insulin is an important hormone in maintaining glucose homeostasis by coordinating the glucose absorption in peripheral tissues and hepatic glucose production. In insulin sensitive tissues, insulin triggers the exocytosis of glucose transporter, enhances the expression of glycolytic enzymes and suppresses the enzymes involved in gluconeogesis. The action of insulin is initiated by binding to its cognate receptor (IR) and activation of the receptor's intrinsic protein tyrosine kinase activity, resulting in the phosphorylation of tyrosine residues located in the cytoplasmic domain. The activated receptor, in turn, recruits and phosphorylates a panel of substrate molecules including IRS-1 and IRS-2. Tyrosine phosphorylated IRS-1/2 recruit the PI 3-kinase to the plasma membrane, where it generates the essential lipid second messenger PIP3, an essential lipid second messenger, which subsequently activates PDK1, PKB/Akt, and PK Cζ and λ isoforms etc. One of the major targets of activated Akt is GSK-3. Akt phosphorylation of GSK leads to its inactivation and glycogen synthesis upregulation. Akt also regulates the insulin-stimulated translocation of the glucose transporter GLUT-4 to the plasma membrane, resulting in increased glucose uptake. Impairment of components in the pathway often leads to disorders like type 2 diabetes (T2D), which is characterized in chronic hyperglycemia and progressive β-cell failure with insufficient insulin output.

Diabetes mellitus (DM) is a metabolic disease with increasing prevalence. Since the decline of pancreatic β-cell function is the major reason for all type 1 diabetes (T1D) and exacerbate type 2 diabetes (T2D) patients, maintaining sufficient circulating insulin thus represents the primary goal in treating DM. Impaired insulin secretion (β-cell), increased hepatic glucose production (liver), and decreased peripheral (muscle) glucose utilization constitute the traditional primary defects responsible for the development and progression of type 2 diabetes mellitus. Currently, the management of type 2 diabetes focuses on glucose control via lowering of blood glucose and hemoglobin Alc(lcHbAlc) with various pharmacological agents. Metformin and the thiazolidinediones (TZDs) are insulin sensitizers that inhibit the increased rate of hepatic gluconeogenesis responsible for the elevated rate of basal hepatic glucose production (HGP) in patients with type 2 diabetes. In adipose tissue, the TZDs also are insulin sensitizers, exerting a potent antilipolytic effect. See Gastaldelli et al., J Clin Endocrinol Metab 91:806-812, 2006 and Gastaldelli et al., Am J Physiol Endocrinol Metab 292:E871-883, 2007. Additionally, the TZDs have been shown to improve and preserve β-cell function. In recent years, treatment strategies have focused on the development of novel therapeutic options that affect many of against the defects contributing to T2D and provide a durable glucose control through a blunting of disease progression. Similar to the patients with T1D, insulin therapy is now recognized as a customary treatment in advanced T2D patients when glycemic control is suboptimal. Discard of its relative effectiveness of glycemic control in T2D patients, subcutaneous insulin injection has suffered from drawbacks including, tissue irritation, infection on injection sites, inconvenience and variation of insulin delivery rate. Therefore, the identification of orally active small molecules that are able to mimic insulin's effect might lead to a better therapy for both DM patients.

Wilcke et al., WO 2008/008033 provides napthoquinones. It also refers to the treatment and control of diabetes, insulin resistance, and hyperglycemia. However, there is a need to identify improved methods and compositions.

SUMMARY

The disclosure relates to methods of managing blood sugar levels and compositions related thereto. In certain embodiments, the disclosure relates to methods of treating or preventing diabetes, insulin resistance, or hyperglycemia comprising administering to a subject diagnosed with, at risk of, or exhibiting symptoms of diabetes, insulin resistance, or hyperglycemia a pharmaceutical composition comprising a 1,4-napthoquinone derivative. In certain embodiments, the 1,4-napthoquinone derivative is a compound of formula I

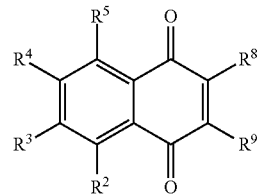

formula I or pharmaceutically acceptable salts thereof wherein, $R^2$ and $R^5$ are not hydroxy or alkoxy;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^6$;

$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^6$;

$R^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^6$;

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$;

$R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^8$ and $R^9$ and the atoms which they bond to form a 5 to 7 membered heterocyclic ring optionally substituted with one or more, the same or different $R^{10}$; or $R^8$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^{10}$;

$R^9$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the 1,4-napthoquinone derivative is any compound disclosed herein substituted with one or more, the same or different, substituent. Other examples include 2-aminonaphtho[2,3-d]thiazole-4,9-dione optionally substituted with one or more, the same or different, substituent; 2-(phenylamino)naphtho[2,3-d]thiazole-4,9-dione optionally substituted with one or more, the same or different, substituent; 5,8-dioxo-5,8-dihydronaphthalen-1-yl acetate optionally substituted with one or more, the same or different, substituent; 5,8-dioxo-5,8-dihydronaphthalene-1,4-diyl diacetate optionally substituted with one or more, the same or different, substituent; 2,3-dichloronaphthalene-1,4-dione substituted with one or more, the same or different.

In certain embodiments, the subject is diagnosed with Type 1 or Type 2 diabetes. In certain embodiments, the subject is diagnosed with having decreased sensitivity to insulin.

In certain embodiments, compounds disclosed herein are administered in combination with insulin.

In certain embodiments, the disclosure relates to uses of compounds disclosed herein in the production of a medicament for the treatment or prevention of diabetes, insulin resistance, or hyperglycemia.

(A) DDN and CSN activate IR and its downstream signaling in CHO-IR cells. CHO-IR cells were treated with insulin (100 nM) or various 1,4-Naphthoquinone derivatives (5 µM) for 15 min. The cell lysates were analyzed by immunoblotting with anti-phospho-IR antibodies, or immunoprecipitated by PY20 and analyzed using anti-IR and anti-IRS-1, respectively. (B) DDN and CSN induce IR phosphorylation in a dose-dependent manner. CHO-IR cells were treated with the small compounds at different concentrations for 15 min, and the IR phosphorylation was monitored by immunoprecipitation and immunoblotting. (C) DDN, CSN induce IR phosphorylation in a time-dependent manner. CHO-IR cells were treated with DDN (5 µM), CSN (5 µM), and insulin (10 nM) for various times, and the IR phosphorylation was monitored by immunoprecipitation and immunoblotting. (D) DDN and CSN induce IR phosphorylation and its downstream signaling in a dose-dependent manner. CHO-IR cells were treated with various concentrations of DDN or CSN for 30 min, or insulin for 15 min, and the IR phosphorylation and its downstream signaling were monitored by immunoprecipitation and immunoblotting. (E) DDN and CSN cannot induce IGF-1R or EGFR phosphorylation. CHO-IGF-1R or HEK293 cells were treated with EGF (100 nM), IGF-1 (100 nM), DDN (10 µM) or CSN (10 µM) for 15 min. The cell lysates were analyzed by immunoblotting with anti-pIGF-1R and anti-pEGFR.

Figures 1, 3:
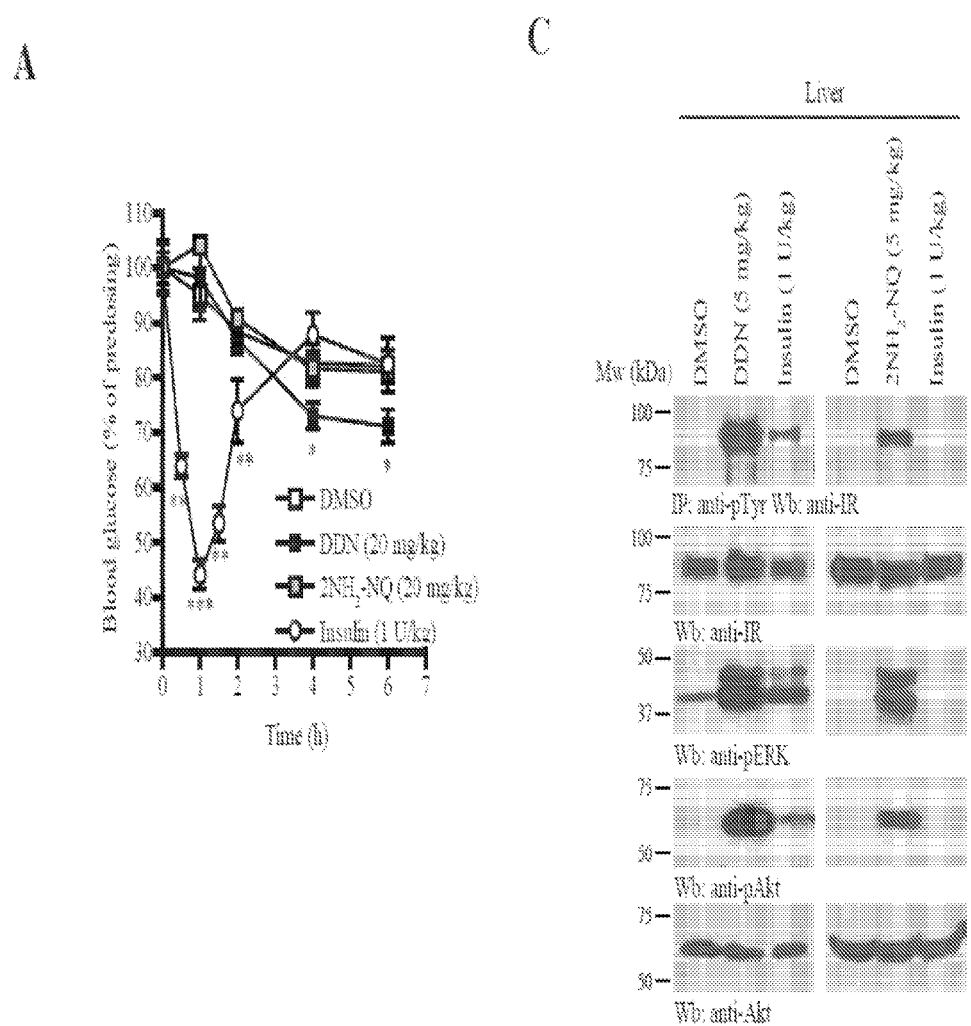
Figures 2, 3:
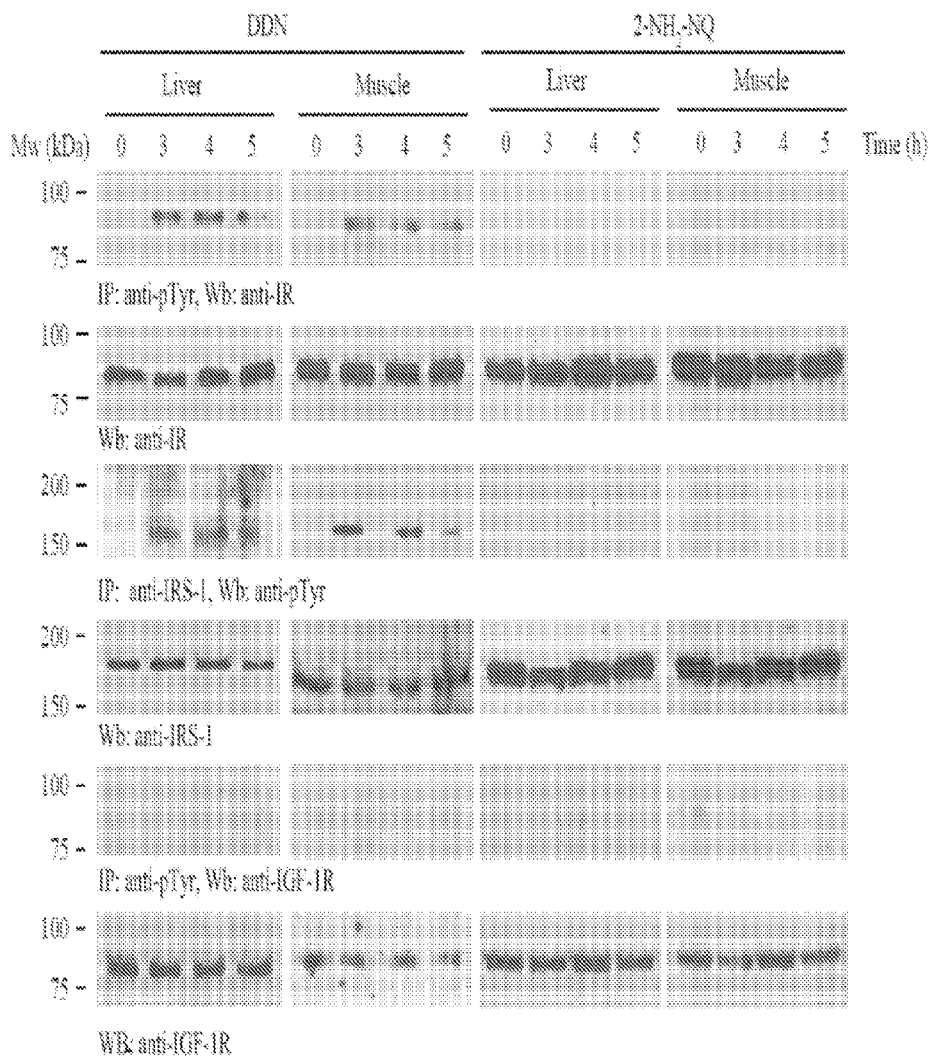

FIG. 3 shows data suggesting DDN activates insulin signaling pathways in vivo and possesses hypoglycemic activity. (A) DDN reduces blood glucose in C57BL/6J mice. C57BL/6J mice were starved for 12 h and then orally administrated with vehicle (0.5% methylcellulose), DDN (20 mg/kg) or the inactive analogue 2NH2-NQ (20 mg/kg). Human insulin (1 U/kg) was injected intraperitoneally as a positive control. Blood glucose was monitored before and after dosing at various time points as indicated (*: $P<0.05$, : $P<0.01$; *: $P<0.001$, n=10-13, Two-way ANOVA vs vehicle). (B) DDN provokes IR phosphorylation and its downstream signaling in C57BL/6J mice. Three month-old C57BL/6J mice were starved for 12 h and then orally administrated with vehicle (0.5% methylcellulose), DDN (20 mg/kg) or 2NH2-NQ (20 mg/kg). Cell lysates were prepared from liver and muscle tissues collected at 3, 4, and 5 h after drug administration and analyzed by immunoprecipitation and immunoblotting. (C) DDN quickly activates IR phosphorylation and its downstream signaling. Three-month-old C57BL/6J mice were starved for 12 h and then injected with vehicle, 5 mg/kg DDN or 5 mg/kg 2NH2-NQ through vena cava. After 5 min, the liver was collected and analyzed by immunobloting using specific antibodies.

Figure 4:
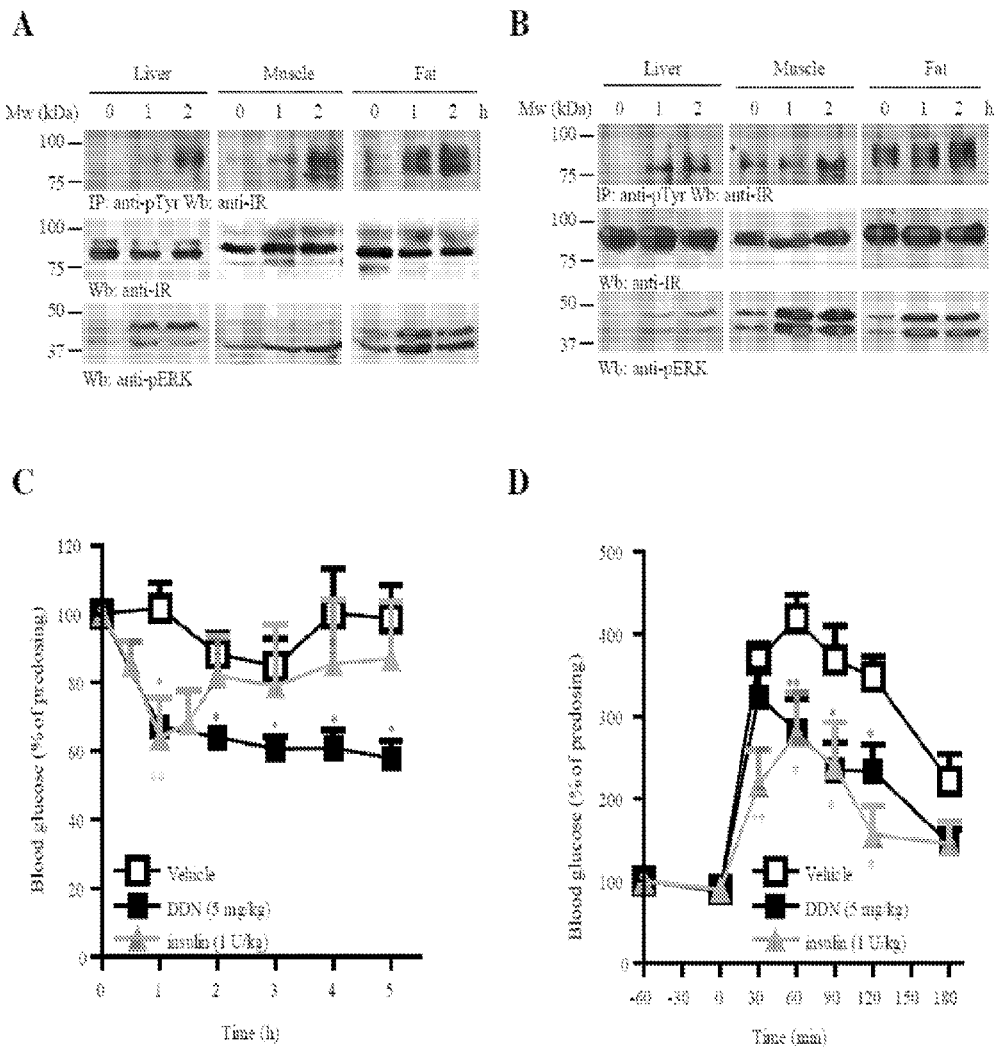

FIG. 4 shows data suggesting DDN displays hypoglycemic function in diabetic mouse models. (A) DDN activates insulin signaling in db/db mice. Three-month-old mice were starved for 12 h and then orally administrated with vehicle (0.5% methylcellulose) or DDN (5 mg/kg). Cell lysates were prepared from liver and muscle tissues collected at 1 and 2 h after drug administration and analyzed by immunoprecipitation and immunoblotting. (B) DDN activates insulin signaling in ob/ob mice. Three-month-old mice were starved for 12 h and then orally administrated with vehicle (0.5% methylcellulose) or DDN (5 mg/kg). Cell lysates were prepared from liver and muscle tissues collected at 1 and 2 h after drug administration and analyzed by immunoprecipitation and immunoblotting. (C) Hypoglycemic function of DDN in db/db mice. The animals were starved for 12 h and then orally injected with vehicle (0.5% methylcellulose) or DDN (5 mg/kg). Human insulin (1 U/kg) was injected intraperitoneally as a positive control. Blood glucose was monitored before and after drug administration at 1-hour intervals (*: $P<0.05$, **: $P<0.01$, n=5, Two-way ANOVA vs vehicle). (D) DDN improves the glucose tolerance in ob/ob mice. The animals were starved for 12 h and then orally dosed with vehicle (0.5% methylcellulose) or DDN (5 mg/kg). Human insulin (1 U/kg) was injected intraperitoneally as a positive control. A bonus of glucose (2 gm/kg) was injected intraperitoneally 1 hour later. Blood glucose was measured at 30-min intervals (*: $P<0.05$, **:$P<0.01$, n=5, Two-way ANOVA vs vehicle control).

Figure 5:
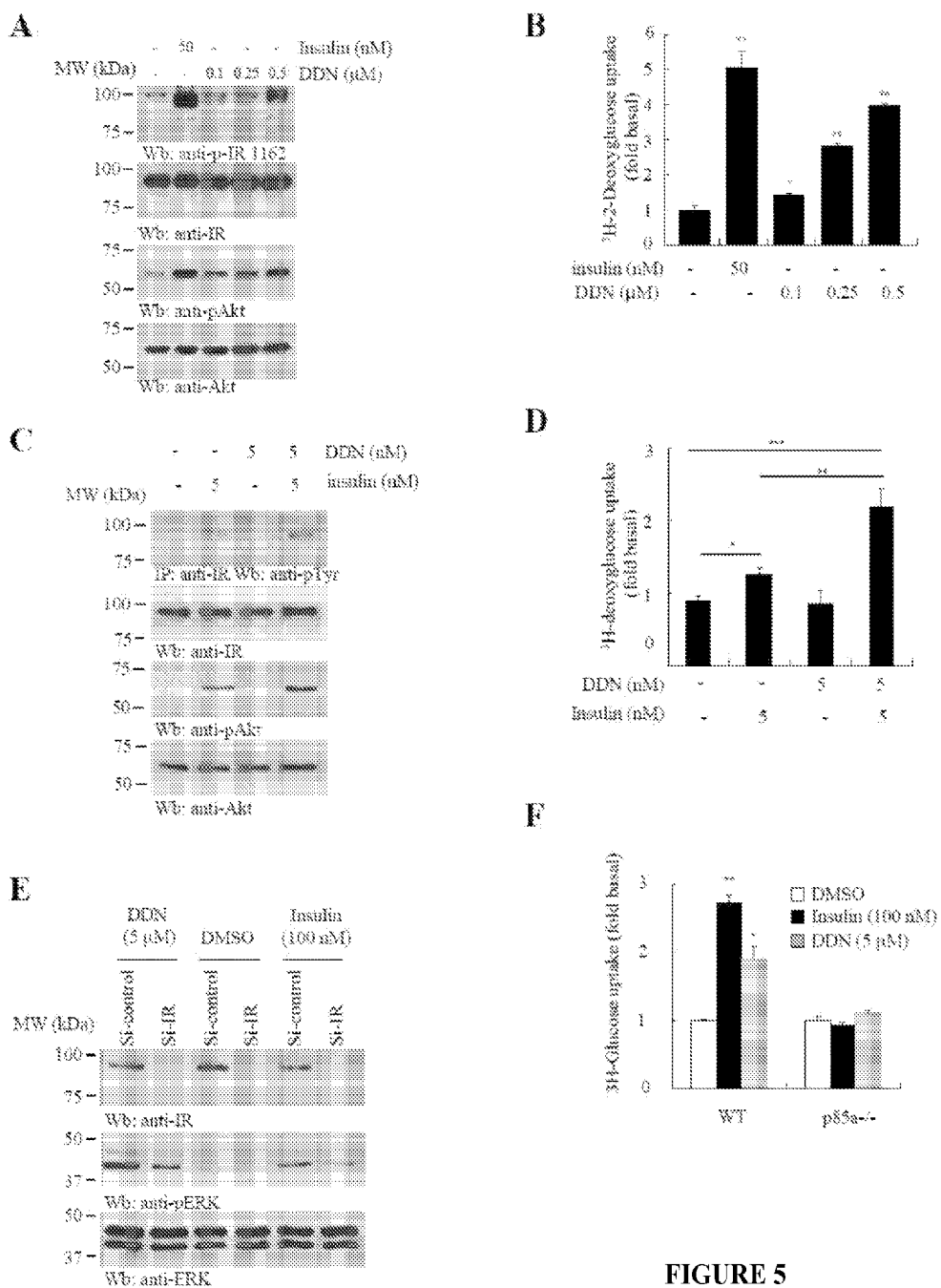

FIG. 5 shows data suggesting DDN enhances cellular glucose uptake (A) DDN provokes IR signaling in differentiated 3T3-L1 adipocytes. The 3T3-L1 cells were stimulated with insulin (50 nM) for 15 min or DDN (0.1, 0.25, 0.5 µM) for 30 min. Insulin signaling in the cell lysates were tested by immunoblotting. (B) DDN stimulates glucose uptake. Differentiated 3T3-L1 adipocytes were stimulated with insulin (50 nM) for 15 min or DDN (0.1, 0.25, 0.5 µM) for 30 min. [3H]2-deoxyglucose was then added, and the cells were further incubated for 10 min. [3H]2-deoxyglucose uptake by adipocytes was measured by scintillation counting (*: $P<0.05$ **: $P<0.01$ vs control, Student's t-test, n=3). (C) DDN synergizes insulin's signaling. Differentiated 3T3-L1 adipocytes were stimulated with 5 nM insulin, 5 nM DDN, or a combination of the two drugs. Cell lysates were then prepared for Western blot using specific antibodies as indicated. (D) DDN synergizes insulin's activity in promoting glucose uptake. Differentiated 3T3-L1 adipocytes were stimulated with 5 nM insulin, 5 nM DDN, or a combination of the two drugs. 3H-2-deoxyglucose was then added, and the cells were further incubated for 10 min. 3H-2-deoxyglucose uptake by adipocytes was measured by scintillation counting (*: $P<0.05$; **: $P<0.01$, Student's t-test, n=3). (E) IR is necessary for DDN to induce ERK phosphorylation. Differentiated 3T3-L1 adipocytes were transfected with control siRNA or siRNA against IR. The cells were then stimulated with insulin (100 nM) for 15 min or DDN (5 µM) for 30 min. Cell lysates were analyzed by Western blot. (F) The glucose uptake induced by DDN in p85α knockout MEF cells. Wild-type and p85α−/− MEF cells were treated with 100 nM insulin for 15 min or 5 µM DDN for 30 min. The uptake of 3H-2-deoxyglucose was monitored by liquid scintillation counting (*: $P<0.05$; **: $P<0.01$ vs control, Student's t-test, n=3).

Figure 6:
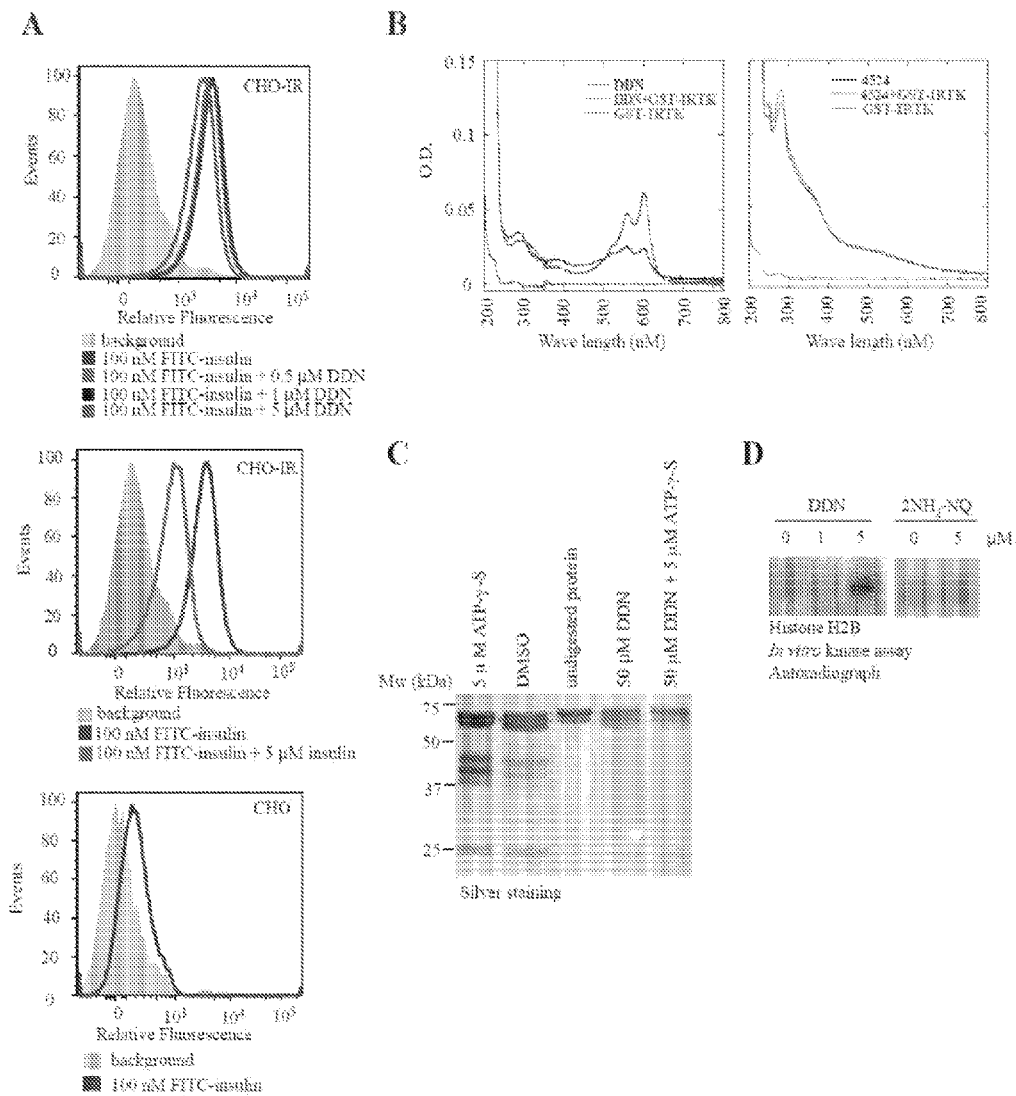

FIG. 6 shows data suggesting DDN interacts and activates the insulin receptor (A) DDN does not complete with insulin for IR binding site. FITC-insulin was incubated with CHOIR cells in the presence of various concentrations of DDN (top panel) or unlabelled insulin (Middle panel). Parental CHO cells were used as a negative control (bottom panel). The fluorescence-labeled cells were analyzed on flow cytometry. (B) DDN binds to IRTK. UV-visible spectra were scanned from 200 to 800 nm for IRTK fragment in the presence of DDN or its analogue. When DDN binds to IRTK, it elicits the absorption alteration at 560 and 602 nm. (C) DDN protects IRTK from proteolysis. GST-IRTK was subjected to limited trypsin digestion in the presence of DDN (50 µM), ATP-γ-S (5 µM) or both. The reaction mixture was resolved by SDS-PAGE, followed by silver staining (D) DDN increases IRTK activity in vitro. Recombinant GST-IRTK was incubated with different concentrations of DDN or its inactive analogue 2NH2-NQ and the kinase activity of IRTK was examined by monitoring the phosphorylation of histone H2B using autoradiography.

Figures 1, 7:
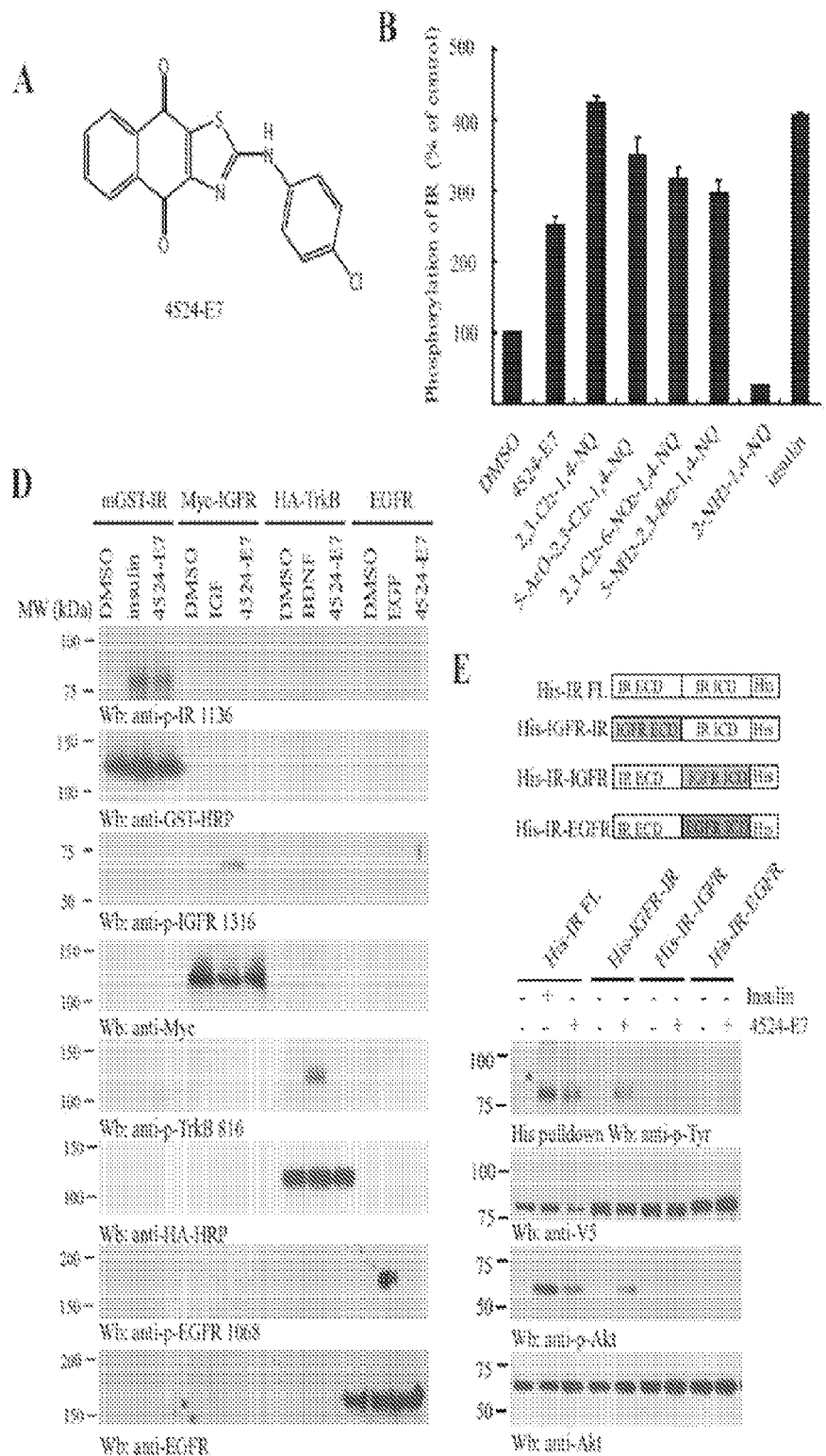
Figures 2, 7:
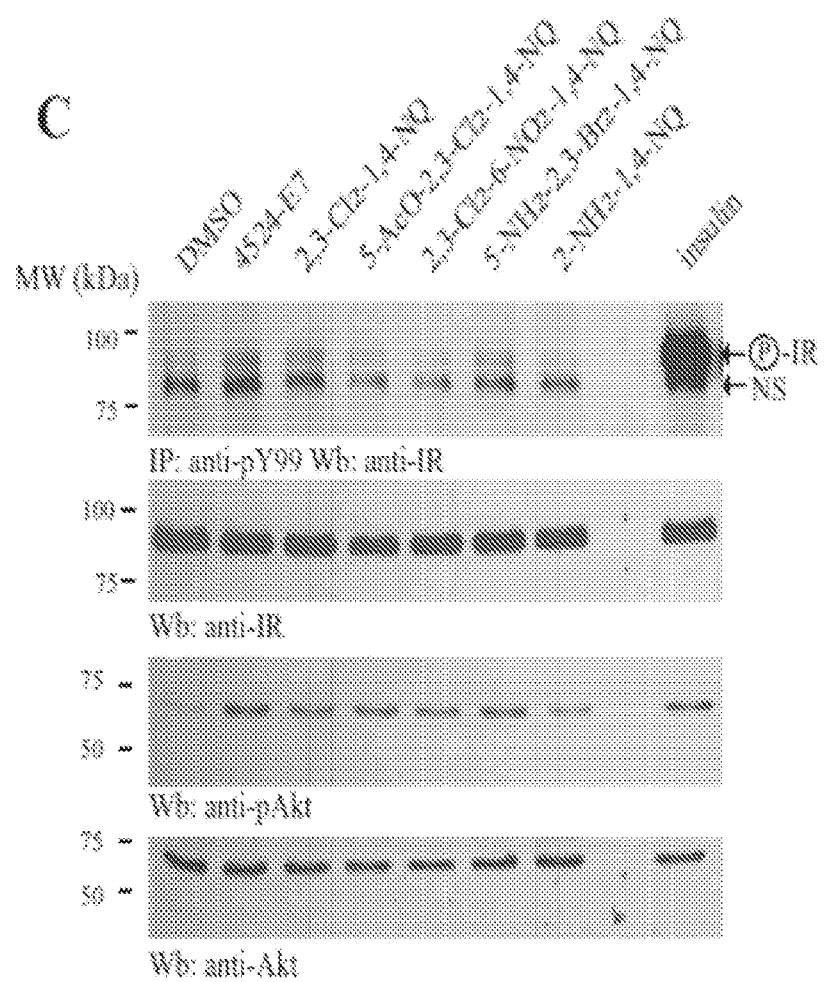

FIG. 7 shows data suggesting 1,4-naphthoquinone compounds stimulate IR phosphorylation in CHO-IR cells. (A) Chemical structure of 4524-E7. (B) Effect of 4524-E7 and other 1,4-naphthoquinone derivatives on IR phosphorylation in CHO-IR cells. CHO-IR cells were cultured in 96-well plates and treated with 5 µM compounds for 15 min at 37 C. Cells were lysed, and IR phosphorylations were tested by ELISA. The IR phosphorylation activities of the tested compounds were expressed as a percentage of the vehicle. (C) 4524-E7 and 1,4-naphthoquinone derivates activate IR and its downstream signaling in CHO-IR cells. CHO-IR cells were treated with insulin (100 nM) or compounds (5 µM) for 15 min. The cell lysates were analyzed by immunoblotting with various indicated antibodies. The phosphorylated IR was immunoprecipitated using PY20 and analyzed by immunoblotting with anti-IR13 antibody. (D) 4524-E7 does not activate IGF-1R, TrkB or EGFR. HEK293 cells were transfected with GST-IR, Myc-IGF-1R, HA-TrkB, or pcDNAEGFR, followed by treatment with insulin (100 nM), IGF-1 (100 nM), BDNF (50 ng/ml), EGF (50 ng/ml) for 15 min or 4524-E7 (5 µM) for 30 min. The phosphorylation of each receptor was determined by Western blot using specific antibodies as indicated. (E) 4524-E7 activates IR through its ICD. Upper panel: Diagram of chimaeric receptors. Lower panel: His-tagged wild-type IR, IGFR-IR, IR-IGFR, and IR-EGFR constructs were transfected into CHO cells followed vehicle or 5 µM 4524-E7 treatment for 30 min. Then the cells were lysated and the transfected receptor fused to His tag were pulled down with Ni+ beads, followed by western blot against anti-p-Tyr and anti-His. The cell lysates were tested with anti-p-Akt and anti-Akt.

Figures 1, 8:
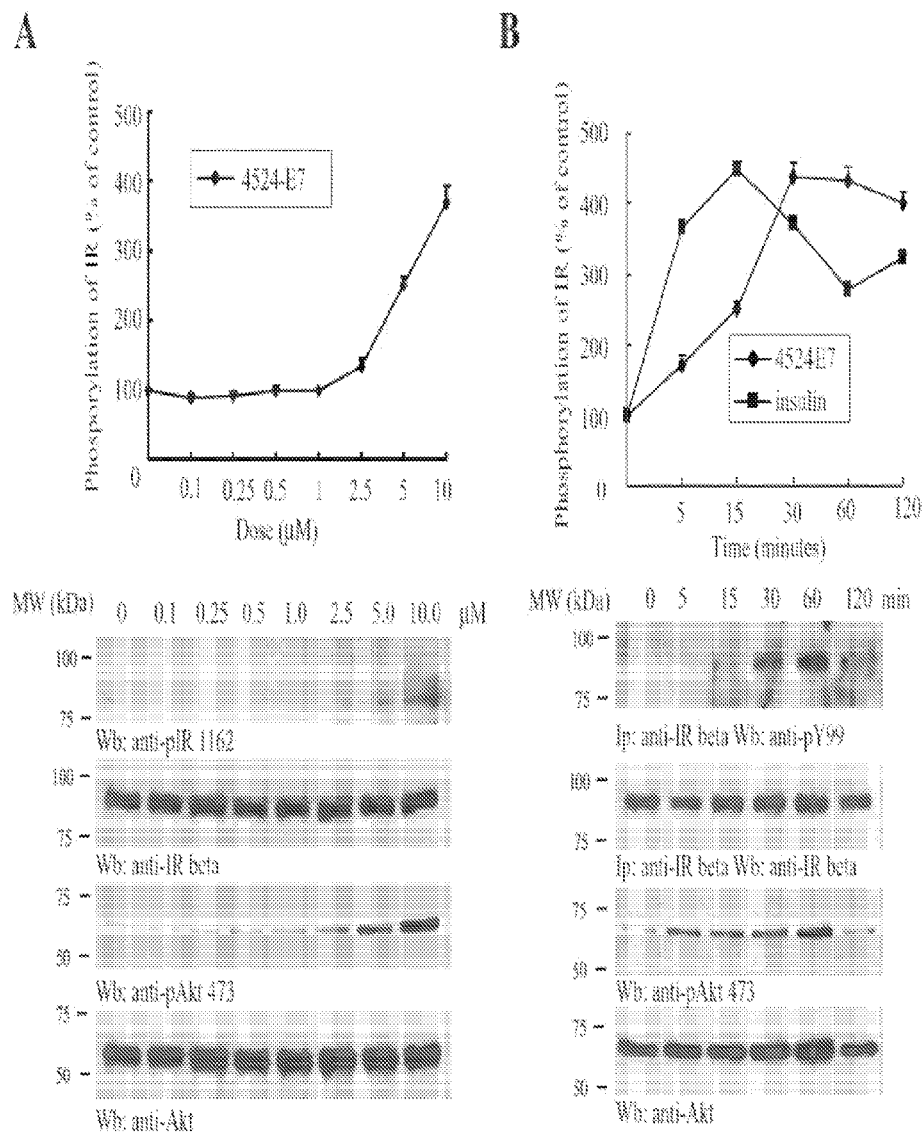
Figures 2, 8:
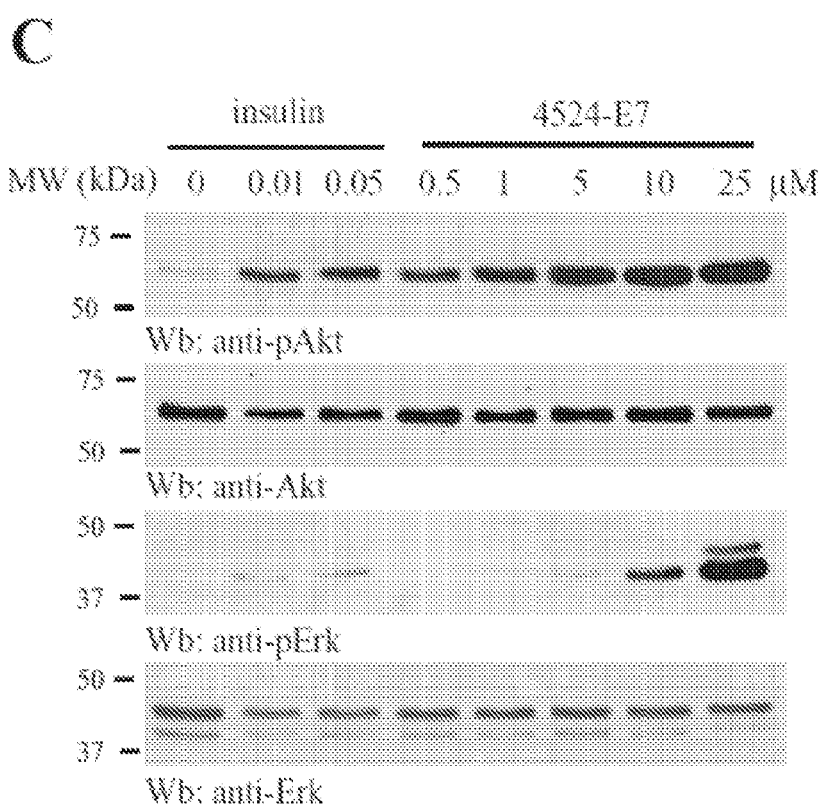

FIG. 8 shows data suggesting 4524-E7 activates insulin signaling pathway. (A) 4524-E7 induces IR phosphorylation in a dose-dependent manner. CHO-IR cells were treated with various concentrations of 4524-E7 for 15 min, and IR phosphorylation was monitored by ELISA (1st panel) and Western blot (2nd to 5th panels). (B) Kinetics of 4524-E7-triggered IR phosphorylation. CHO-IR cells were treated with 4524-E7 (5 µM) or insulin (50 nM) for various time points, and the IR phosphorylation was analyzed by ELISA (1st panel) and Western blot (2nd to 5th panels). (C) 4524-E7 activates Akt and MAPK signaling pathways in a dose-dependent manner. CHO-IR cells were treated with insulin or 4524-E7 at various concentrations for 15 min. Cell lysates were then collected and the activation of Akt and Erk were examined by Western blot.

Figures 1, 9:
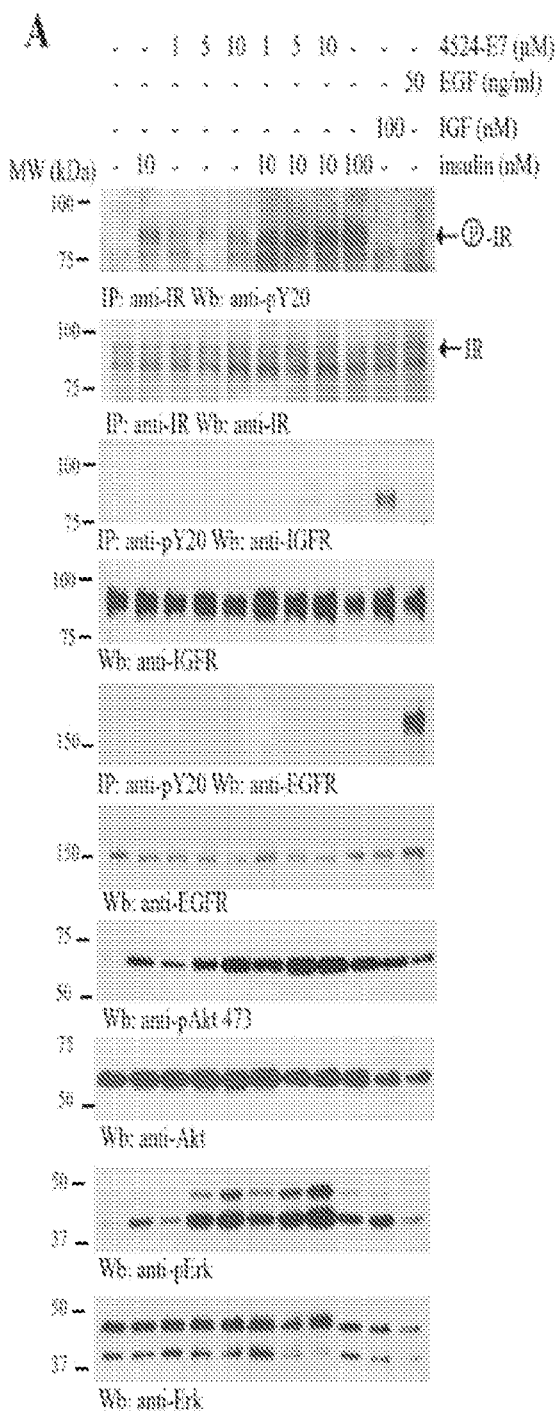
Figures 2, 9:
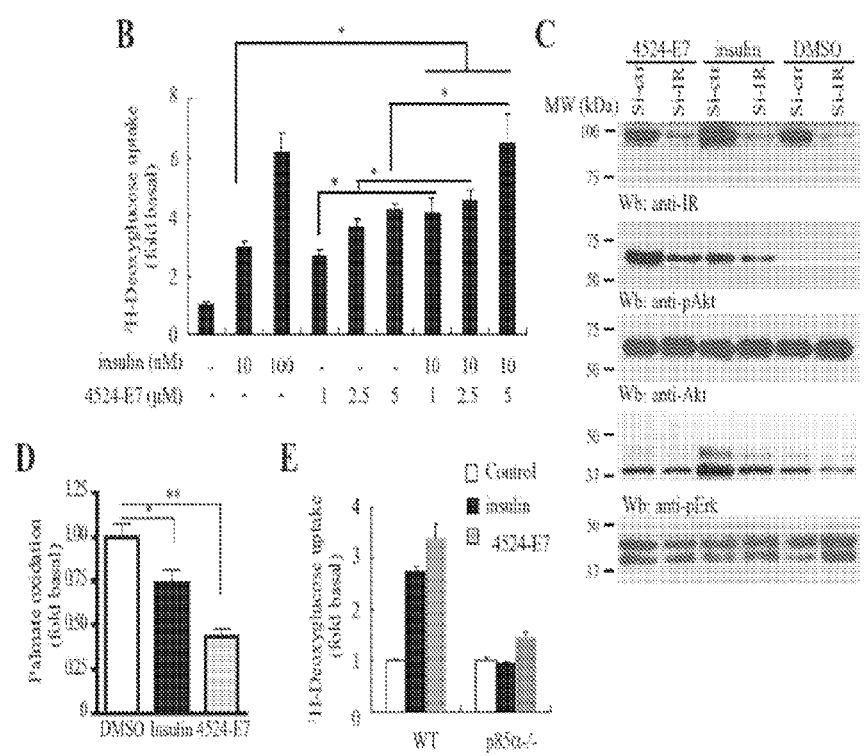

FIG. 9 shows data suggesting 4524-E7 promotes glucose uptake. (A) 4524-E7 activates IR phosphorylation and its downstream signaling in 3T3-L1 adipocytes. Differentiated 3T3-L1 adipocytes were incubated with different concentrations of insulin and 4524-E7 for 15 min. The cells were lysed, and immunoprecipitated with PY20, and followed by Western blot using specific antibodies. (B) 4524-E7 stimulates glucose uptake in 3T3-L1 adipocytes. Differentiated 3T3-L1 adipocytes were stimulated with insulin for 15 min or 4525-E7 for 30 min. [3H]2-deoxyglucose was added, and the cells were further incubated for 10 min. The amount of [3H]2-deoxyglucose taken by adipocytes was measured. (C) 4524-E7 inhibits fatty acid oxidation. Oxidation of 3H-palmitate was measured in differentiated 3T3-L1 adipocytes after stimulation with DMSO, 100 nM insulin or 5 μM 4524-E7. Results were normalized to DMSO-treated cells and expressed as mean±S.E.M. (*: $P<0.05$; **: $P<0.01$, Student's t-test, n=3). (D) IR knockdown in adipocytes decreases IR signaling by 4524-E7. Differentiated adipocytes were transfected with control RNA (si-Ctr) or siRNA against IR (si-IR) for 2 days, followed 5 μM 4524-E7 or insulin (100 nM) treatment. Cells lysates were collected and analyzed by Western blot. (E) The glucose uptake induced by 4524-E7 in p85α knockout MEF cells. Wild-type and p85α-/- MEF cells were treated with 100 nM insulin for 15 min or 5 μM 4524-E7 for 30 min. The uptaken [3H] 2-deoxyglucose was monitored by liquid scintillation counter. Results were expressed as mean±S.E.M. (*: $P<0.05$; **: $P<0.01$, Student's t-test, n=3).

Figures 1, 10:
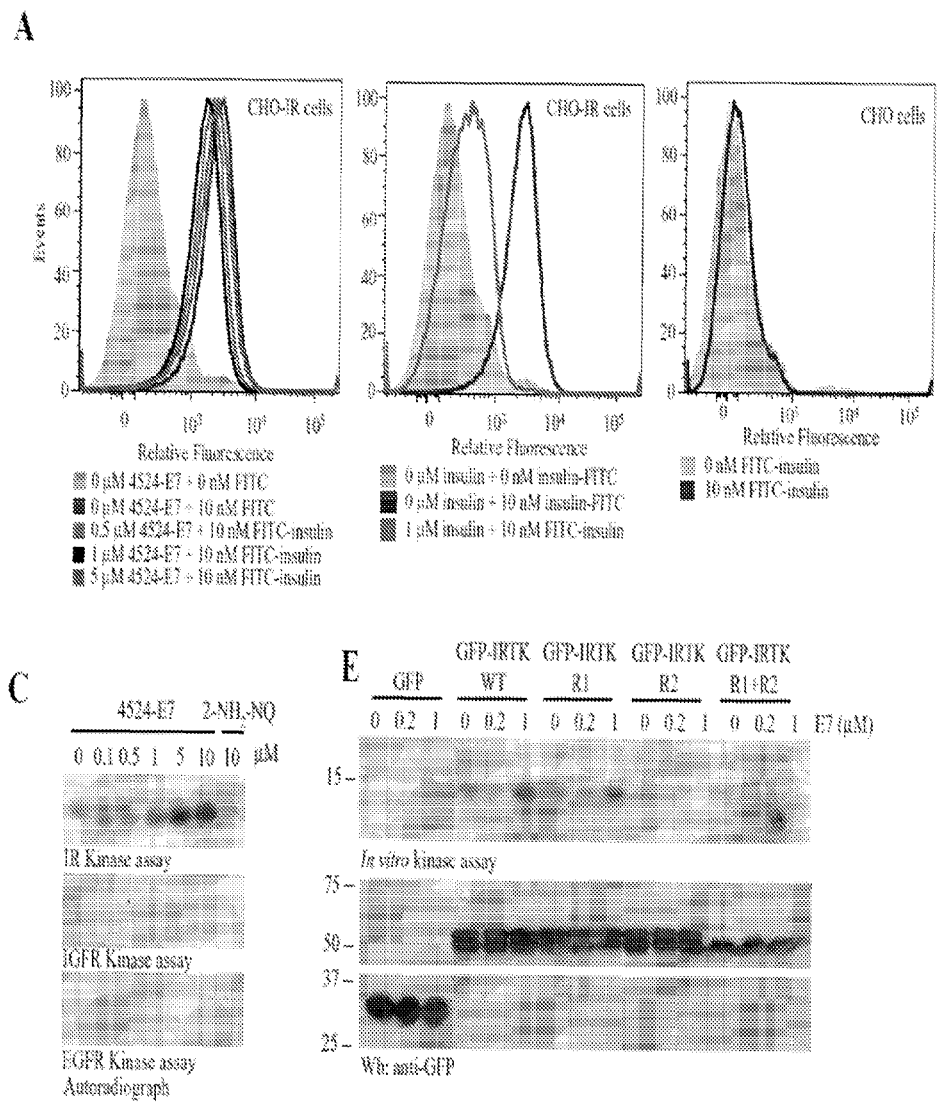
Figures 2, 10:
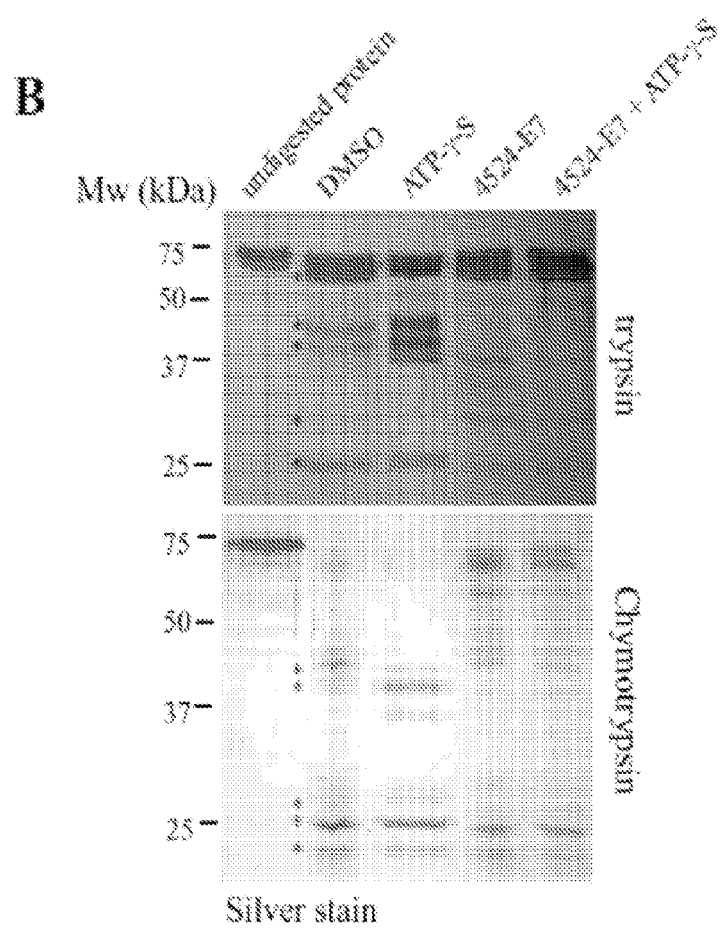

FIG. 10 shows data suggesting 4524-E7 interacts with insulin receptor to activate it. (A) 4524-E7 does not affect insulin binding to IR. FITC-insulin was incubated with CHO-IR cells in the presence of various concentrations of 4524-E7 (Top panel) or unlabelled insulin (Middle panel). Parental CHO cells were used as a negative control (Bottom panel). The fluorescence-labeled cells were analyzed on flow cytometry. (B) 4524-E7 protects IRTK from proteolysis. GST-IRTK was subjected to limited trypsin or chymotrypsin digestion in the presence of 4524-E7 (50 μM), ATPyS (5 μM) or both at 37° C. for 5 min. The reaction mixture was resolved by SDS-PAGE, followed by silver staining Cleaved fragments were asterisked. (C) 4524-E7 increases IRTK activity in vitro. Recombinant GST-IRTK, GST-IGFRTK, and GST-EGFRTK were incubated with different concentrations of 4524-E7 or 10 μM 2—NH2-NQ and the kinase activity was examined by monitoring the phosphorylation of histone H2B. (E) In vitro kinase activity of various IRTK/IGF-1R kinase hybrids. The GFP-tagged kinases were expressed in HEK293, immunoprecipitated and incubated with different concentrations of 4524-E7 as indicated. The kinase activity is revealed by the phosphorylation of histone H2B (upper panel). Expressions of the kinases were also verified (lower panel).

Figure 11:
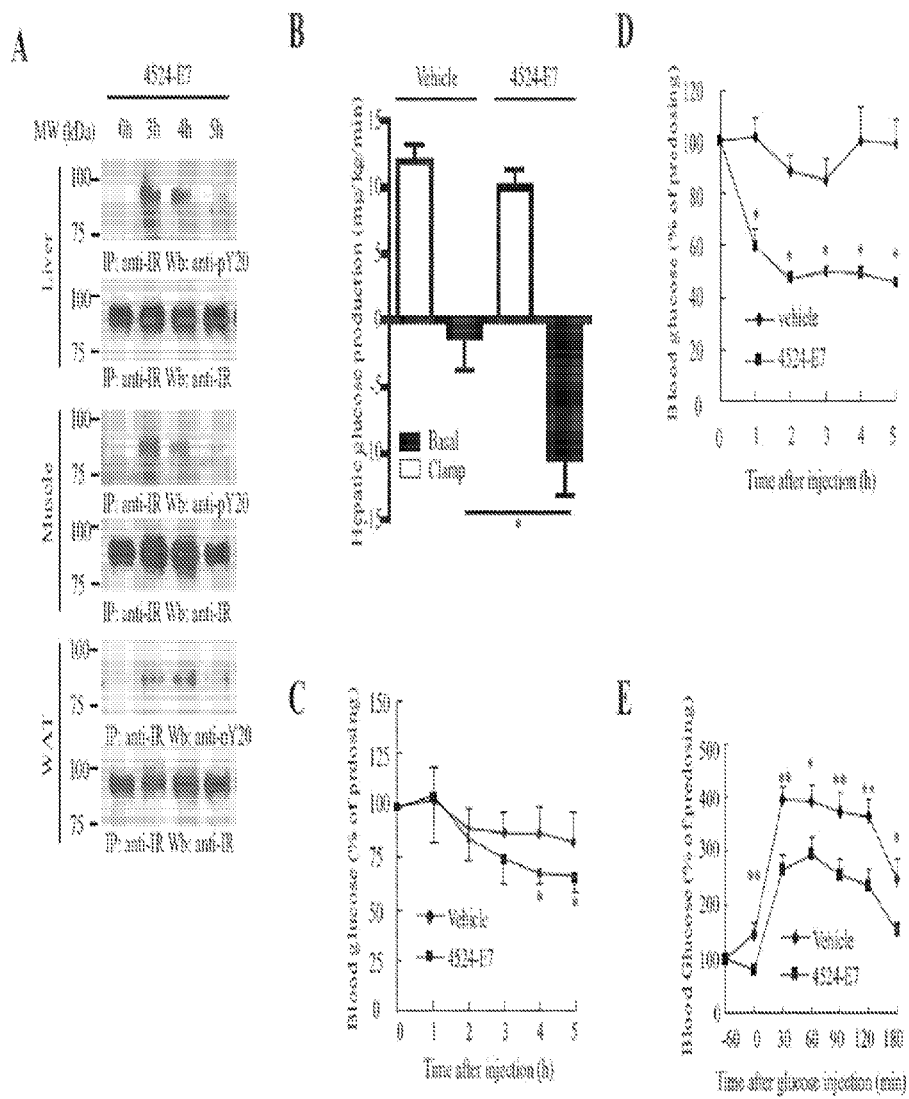

FIG. 11 shows data suggesting 4524-E7 displays anti-diabetic efficacy in mouse models of diabetes. (A) 4524-E7 provokes IR phosphorylation in various tissues of mice. Three-month-old C57BL/6J mice were starved for 12 h and then dosed with vehicle (0.5% methylcellulose) or 4524-E7 (20 mg/kg). Cell lysates from liver, muscle, and WAT were prepared at 3, 4, and 5 h after drug administration and analyzed by immunoblotting. (B) Basal and insulin-stimulated hepatic glucose production rates were measured by hyperinsulinemic-euglycemic clamp. The negative values implicate that insulin caused a net uptake of glucose into liver (*: $P<0.05$, Student's t-test n=5). (C) Hypoglycemic effect of 4524-E7 in C57BL/6J mice. C57BL/6J mice were starved for 12 h and then orally administrated with vehicle (0.5% methylcellulose) or 4524-E7 (5 mg/kg). Blood glucose was monitored at different time points as indicated (n=8, *: $P<0.05$, two-way ANOVA). (D) Hypoglycemic effect in db/db mice. db/db mice were starved for 12 h and then orally injected with vehicle (0.5% methylcellulose) or 4524-E7 (5 mg/kg). Blood glucose was monitored at different time points as indicated (n=5, *: $P<0.05$, two-way ANOVA). (E) Glucose tolerance test in ob/ob mice. The mice were starved for 12 hours and then orally administrated with vehicle or 4524-E7 (5 mg/kg). A bonus of glucose (2 gm/kg) was injected intraperitoneally 1 hour later. Blood glucose was then measured at 30 min intervals (n=13, *: $P<0.05$; **: $P<0.01$, two-way ANOVA).

Figure 12:
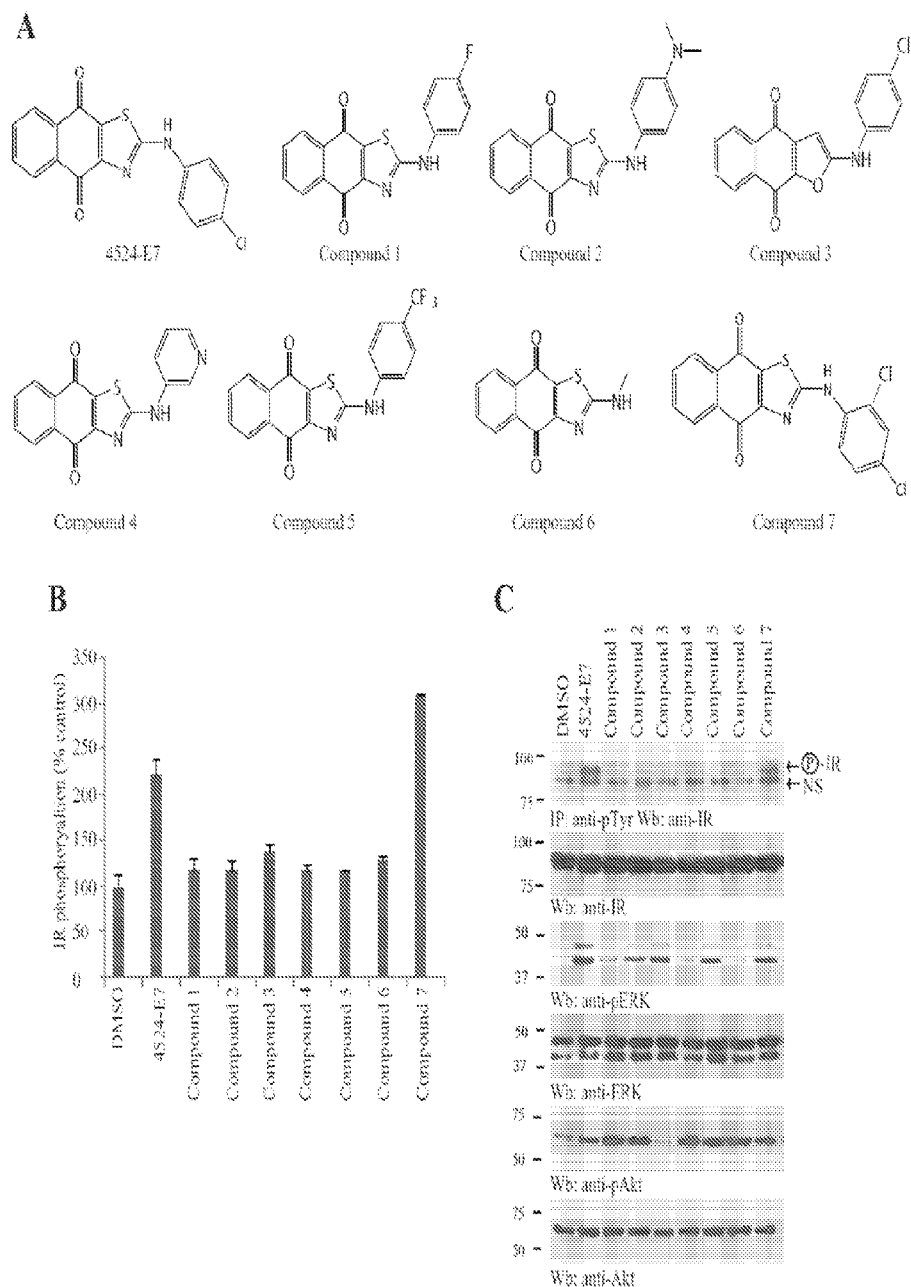

FIG. 12 shows data from an SAR study of 4524-E7. (A) Chemical structures of 4524-E7 derivatives. (B) Effects of 4524-E7 derivatives on IR phosphorylation in CHO-IR cells. CHO-IR cells were treated with different 4524-E7 derivatives (5 μM) for 30 min. The amount of phosphorylated IR was quantified by sandwich ELISA using immobilized anti-phosphotyrosine (pY20) and anti-IR antibodies. The activities of the tested compounds were expressed as a percentage of the control (DMSO). (C) 4524-E7 derivates activate IR and its downstream signaling in CHO-IR cells. CHO-IR cells were treated with compounds (5 μM) for 30 min. The cell lysates were analyzed by immunoblotting using various antibodies as indicated. The phosphorylated IR was immunoprecipitated using PY20 and analyzed by immunoblotting with anti-IR antibody.

DETAILED DESCRIPTION

Terms

When describing the compounds for use in the disclosure, the terms used are to be construed in accordance with the following definitions, unless a context dictates otherwise.

As used herein, "alkyl" means a noncyclic straight chain or branched, unsaturated or saturated hydrocarbon such as those containing from 1 to 10 carbon atoms, while the term "lower alkyl" or "C1-4alkyl" has the same meaning as alkyl but contains from 1 to 4 carbon atoms. The term "higher alkyl" has the same meaning as alkyl but contains from 7 to 20 carbon atoms. Within certain embodiments, alkyl may be a lower alkyl or higher alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH3).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined attached through an amino bridge. An example of an alkylamino is methylamino, (i.e., —NH—CH3).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)2alkyl) such as mesyl and the like, and "Arylsulfonyl" refers to an aryl attached through a sulfonyl bridge (i.e., —S(=O)2aryl).

"Alkylsulfamoyl" refers to an alkyl as defined above attached through a sulfamoyl bridge (i.e., —NHS(=O)2alkyl), and an "Arylsulfamoyl" refers to an alkyl attached through a sulfamoyl bridge (i.e., (i.e., —NHS(=O)2aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet. The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

Compounds

In certain embodiments, the disclosure relates to compounds disclosed herein. In a typical embodiment, the compound comprises formula I

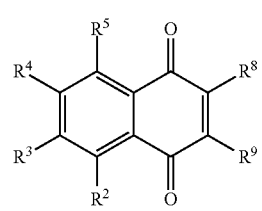

formula I or pharmaceutically acceptable salts thereof wherein, $R^2$ and $R^5$ are not hydroxy or alkoxy;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^6$;

$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^6$;

$R^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^6$;

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$;

$R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^8$ and $R^9$ and the atoms which they bond to form a 5 to 7 membered heterocyclic ring optionally substituted with one or more, the same or different $R^{10}$; or $R^8$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^{10}$;

$R^9$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^2$ and/or $R^5$ are hydroxy substituted with formyl, wherein formyl is substituted with $R^7$.

In certain embodiments, $R^2$ is hydroxy substituted with formyl, wherein formyl is substituted with $R^7$.

In certain embodiments, $R^5$ is hydrogen.

In certain embodiments, $R^8$ is a halogen.

In certain embodiment, $R^9$ is halogen.

In certain embodiments, the compound is selected from 5,8-diacetyloxy-2,3-dichloro-1,4-naphthoquinone;

5-acetyloxy-2,3-dichloro-1,4-naphthoquinone;

2-((4-chlorophenyl)amino)naphtho[2,3-d]thiazole-4,9-dione, and 2-((2,4-dichlorophenyl)amino)naphtho[2,3-d]thiazole-4,9-dione or salts thereof.

In certain embodiments, the compound of formula I has formula IA,

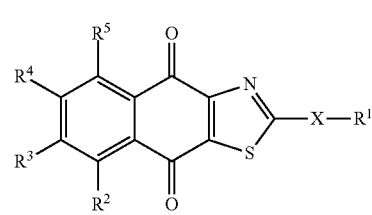

formula IA or pharmaceutically acceptable salts thereof wherein,

X is NH, O, or S;

$R^1$ is alkyl, formyl, carboxy, carbamoyl, carbocyclyl, aryl, or heterocyclyl, wherein $R^1$ is optionally substituted with one or more, the same or different, $R^6$;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^6$;

$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^6$;

$R^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^6$;

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is NH.

In certain embodiments, $R^1$ is carbocyclyl, aryl, or heterocyclyl optionally substituted $R^6$.

In certain embodiments, $R^6$ is a halogen.

In certain embodiments, $R^2$ and $R^5$ are not hydroxy or alkoxy.

In certain embodiments, $R^2$ and $R^5$ are hydrogen.

In certain embodiments, the compound of formula I has formula IB,

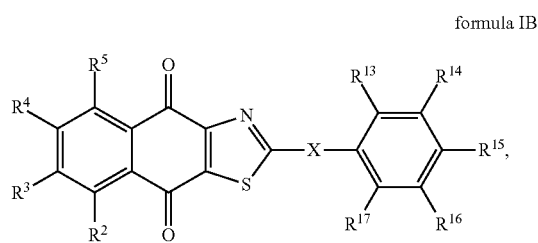

formula IB or pharmaceutically acceptable salts thereof, wherein
X is NH, O, or S;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^6$;

$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^6$;

$R^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^6$;

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$;

$R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{13}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13}$ is optionally substituted with one or more, the same or different, $R^{18}$;

$R^{14}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{18}$;

$R^{15}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{18}$;

$R^{16}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{18}$;

$R^{17}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{17}$ is optionally substituted with one or more, the same or different, $R^{18}$;

$R^{18}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{18}$ is optionally substituted with one or more, the same or different, $R^{19}$; and $R^{19}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^2$, $R^3$, $R^4$, and $R^5$ are hydrogen.

In certain embodiments, X is NH.

In certain embodiments, $R^{13}$ is a halogen.

In certain embodiments, $R^{15}$ is a halogen.

Pharmaceutical Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When the compounds contain a hydrogen-donating heteroatom (e.g. NH), this disclosure contemplates salts and/or isomers formed by transfer of said hydrogen atom to a basic group or atom within the molecule, such as in the case of an amino acid.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087, and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087, and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

For subcutaneous or intravenous administration, the compounds, if desired with the substances customary therefore such as solubilizers, emulsifiers or further auxiliaries are brought into solution, suspension, or emulsion. The compounds of formula I can also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. A barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly(acrylic acid); poly(hydroxyalkylmethacrylates) (for example poly (hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethylcellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Compound Evaluations

A cell-based screening assay was developed with Chinese hamster ovary cells stably transfected with IR (CHO-IR) by using an ELISA to determine the IR tyrosine phosphorylation. 4524-E7 (FIG. 7A) was identified as an effective IR activator. When stimulated with 5 µM of 4524-E7, IR phosphorylation in CHO-IR cells was increased to about 250% of basal level (FIG. 7B). Other 1,4-Napthoquinones that are structurally related to 4524-E7 were evaluated. Four of the derivatives [2,3-Dichloro-1,4-naphthoquinone (2,3-Cl2-1,4-NQ), 5-acetoxy-2,3-dichloro-1,4-Naphthoquinone (5-AcO-2,3-Cl2-1,4-NQ), 2,3-Dichloro-6-Nitro-1,4-Naphthoquinone (2,3-Cl2-6-NO2-1,4-NQ), and 5-amino-2,3-dibromonaphthoquinone (5-NH2-2,3-Br2-1,4-NQ)] were able to induce IR phosphorylation substantially (from ~300% to ~400% of basal level), which was comparable to the insulin-activated IR phosphorylation. In contrast, the analog 2-amino-1,4-Napthoquinone (2—NH2-1,4-NQ) was not active in the assay (FIG. 7B).

2-((4-chlorophenyl)amino)naphtho[2,3-d]thiazole-4,9 (3aH,9aH)-dione (4524-E7) acts as an insulin mimetic. 4524-E7 has selectively activates IR but not IGF-1R or other receptor tyrosine kinases (RTKs). It specifically activates RTKs containing the ICD but not ECD from IR. Switching a motif (1117-1125 a.a.) from IGF-1R kinase domain into IR blunts 4524-E7's agonistic effect on IR. Through binding to the kinase domain of IR, it activates the kinase activity and the downstream Akt and Erk pathways to trigger glucose uptake in differentiated 3T3-L1 adipocytes. In addition, it additively potentiates the activation of IR by insulin. Moreover, it has potent blood glucose lowering effect when administrated orally in normal and diabetic mice models.

2-((4-chlorophenyl)amino)naphtho[2,3-d]thiazole-4,9 (3aH,9aH)-dione (4524-E7) selectively activates IR but no other receptor tyrosine kinases (RTKs) in vitro and in vivo. It also potentiates insulin's ability in provoking IR and its downstream signaling cascades to trigger glucose uptake. In diabetic mice (db/db and ob/ob), oral administration of 4524-E7 significantly lowers blood glucose and improves the glucose tolerance.

4524-E7 strongly and specifically activates IR cascade at 1-2.5 µM, and it is unable to activate other RTKs in this concentration range. A few classes of non-peptidyl IR activators have also been reported with different modes of mechanistic actions. For example, TLK19780 and its derivative TLK16998 are insulin sensitizers, which potentiate the insulin-triggered IR phosphorylation. However, these compounds are inactive when administered alone. We also found that 4524-E7 potentiates insulin's action in promoting IR activation and upregulating glucose uptake (FIG. 9). This additive effect might be a result of differential IR ligand binding sites by insulin and 4524-E7. 4524-E7 does not compete with insulin for IR binding, instead, it binds to the IR kinase domain directly. Hence, IR could simultaneously interact with both insulin on its extracellular domain and 4524-E7 on its intracellular kinase domain. This insulin sensitizing effect by 4524-E7 provides an extra beneficial mechanism for treating T2DM as compared to other reported insulin's sensitizers or insulin mimetics. 4524-E7 displays a higher efficacy in diabetic mice with shorter time needed to lower the blood glucose in db/db than the normal C57/BL6 controls (FIG. 11).

Structurally, DAQ B1, CPD2 and ZL-196 and LD17 belong to the indolyl-dihydroxybezoquinone family, whereas 4524-E7 is a derivative of 1,4-naphthoquinone. Though DAQ B1, CPD2, TLK16998 and 4524-E7 have distinct chemical structures, they all exert the stimulatory activity on the IR β-subunit, which is different from insulin that binds to the α-subunit on the extracellular domain of IR. Presumably, the receptor binding style difference between the small molecules and insulin might result in distinctive effects on the ligand-mediated functions. For instance, DAQ-B1 does not have the mitogenic effect on vascular smooth muscle cells. Thus, it is possible that 4524-E7 may distinguish from insulin in some aspects of physiological actions as well. Indeed, 4524-E7 is not able to induce the proliferation of MCF7 cells, although 4524-E7 provokes prolonged IR signaling as ASPB10-insulin, a mitogenic analog that cause mammary tumors in rats.

CPD2, a second generation of IR activator derived from DAQ-B1, prevents food intake and weight gain when administrated in normal mice. Mice were chronically treated with 4524-E7 for 2 weeks and tested if the compound can inhibit food intake. At dose of 5 mg/kg, food intake and body weight are not significantly changed as compared to vehicle control. Moreover, blood chemistry analysis revealed comparable results between drug-treated mice and vehicle control. Furthermore, no demonstrable toxicity was detected by the pathological examination on all major organs for a two week period. Data herein suggest that 4524-E7 mimics insulin's biological actions by specifically binding to IRTK to increase its kinase activity. It is orally bioactive and lowers blood glucose in normal and insulin-resistant mice through enhancing glucose uptake in insulin sensitive tissue like adipocytes.

DDN, chemical name 5,8-diacetyloxy-2,3-dichloro-1,4-naphthoquinone, is a selective insulin receptor (IR) activator, which interacts directly with the IR tyrosine kinase domain to induce the Akt and ERK phosphorylations. It is also an insulin sensitizer that enhances insulin's action to stimulate glucose uptake. Oral administration of this compound robustly decreases blood glucose in wild-type and diabetic ob/ob and db/db mice.

It has reported that DAQ B1 is an orally active IR ligand with anti-diabetic activity. Zhang et al., Science, 1999, 284, 974-977. Structure-activity relationship study on DAQ B1 derivatives provided mono-indolyl-dihydroxybenzoquinones ZL-196 and LD-17. Lin et al., J Pharmacol Exp Ther, 2007, 323, 579-585. However, these compounds also provoke other RTKs activation including IGF-1R, NGF and EGFR. In contrast, DDN specifically activates IR and its downstream cascades. A few classes of non-peptidyl IR activators have also been reported with different modes of actions. For example, TLK19780 is an insulin sensitizer, which potentiates the insulin-triggered IR phosphorylation. However, it is inactive when administrated alone.

DDN potentiates insulin's action in promoting IR activation and upregulating glucose uptake. This additive effect might be a result of differential IR ligand binding sites by insulin and DDN. DDN does not complete with insulin for IR binding but binds to the IR kinase domain directly. Although it is not intended that embodiments of the disclosure be limited to any particular mechanism, it is believed that IR could simultaneously interact with both insulin on its extracellular domain and DDN on its intracellular kinase domain.

When administrated orally, DDN has hypoglycemic function in both normal and diabetic mice models that the glucose lowering effect could be observed after 1 h administration. It is possible that the metabolites of DDN, in addition to DDN itself, might also possess the hypoglycemic activity in vivo. However, our cell based in vitro studies show that DDN directly binds IR and activates it within 5-15 min, suggesting DDN per se has significant activity in provoking IR activation. Moreover, IR activation in liver and muscle could be observed in 5 min, when DDN is injected into blood stream directly through vena cava. DDN takes shorter time to reduce blood glucose level in db/db mice than in normal C57BL/6 mice.

2,3-Bis-methylsulfanyl-1,4-naphthoquinone (CSN) is also an effective IR activator in vitro. However, it is lethal to the animals when administered in vivo. 1,4-Naphthoquinones are widely distributed phenolic compounds in nature and these naphthoquinones display diverse pharmacological properties. Most of these quinoids belong to DNA intercalating agents. For instance, plumbagin (5-hydroxy-2-methyl-1,4-naphthoquinone) can induce mammalian topoisomerase II-mediated DNA cleavage in vitro. Therefore, they are effective anti-cancer agent against murine fibrosarcoma, P388 lymphocytic leukemia and non-small cell lung cancer cells A549 (19-21). In addition, the semiquinone radicals generated either by one electron reduction or two-electron reduction followed by a subsequent oxidation from quinine by DT-diaphorase damage the thiol groups or nucleophilic moieties of proteins. The oxidative stress induced by these quinone derivatives has been proposed to be responsible for initiation of cellular damage. Conceivably, the metabolites of CSN may covalently modify the thiol groups in many proteins, which may lead to its adverse side effects. In contrast, DDN does not exhibit any intolerable side effects when administrated to animals for two weeks, suggesting DDN and CSN might behave very differently.

EXPERIMENTAL

Animals

Male C57BL/6J mice, male C57BL/KsJ db/db mice, and female C57BL/KsJ ob/ob mice were obtained from the Jackson Laboratory (Bar Harbor, Me.). Adult animals aged 10-12 weeks were used. Mice were housed in environmentally controlled conditions with a 12-h light/dark cycle and had free access to standard rodent pellet food and water. The animal protocols were approved by the Institutional Animal Care and Use Committee (IACUC) of Emory University. Animal care was in accordance with institutional guidelines.

Cells and Reagents

CHO-IR and CHO-IGF-1R cells (a gift from Dr. Nicholas Webster, UCSD) were maintained in Ham's F12 plus 10% fetal bovine serum (FBS), 100 units of penicillin-streptomycin, and 200 ng/ml of G-418. HEK293, mouse NIH 3T3-L1 cells (Xiaonan Wang, Emory University), and Mouse embryonic fibroblasts (MEF) cells were maintained in DMEM with 10% FBS and 100 units of penicillin-streptomycin. All cells were maintained at 37° C. with 5% $CO_2$ atmosphere in a humidified incubator. DDN and 5-acetoxy-2,3-dichloro-1,4-naphthoquinone was from InterBioscreen. For experiments, cells were treated in the appropriate serum-free media containing compounds dissolved in DMSO. Control cells received equivalent amounts of DMSO, and the final concentration of DMSO was always kept below 0.1%. 4524-E7, insulin, and IGF-1, and glutathione S-tranferase (GST)-horseradish peroxidase was from Sigma. [3H] 2-deoxyglucose was purchased from PERKINP. Anti-beta IR and IRS-1 were from Santa Cruz. Anti-phospho-Akt 473, anti-phospho-Erk, and anti-phospho-1R-1146 were from Cell Signaling.

Anti-phosphotyrosine (pY20) was from BD Bioscience. GST-IRTK and His-IR protein were from Invitrogen and R&D, respectively.

Preparation of Derivatives

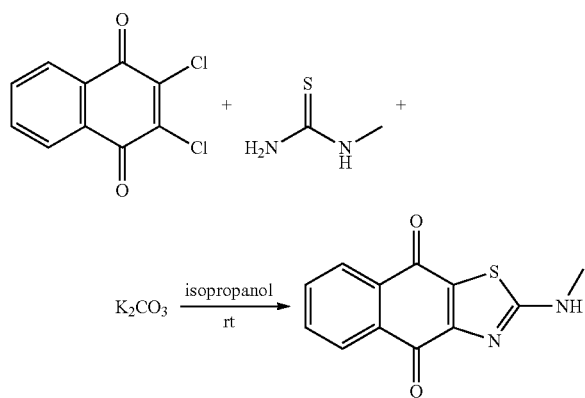

A mixture of 2,3-dichloronaphthalene-1,4-dione 10.0 g (0.044 mol,), 18.0 g K2CO3 (0.13 mol, 3.0 eq) and 1-methylthiourea (0.056 mol, 1.2 eq) in 100 ml isopropanol was stirred at room temperature under N2 for 20 h. After removing all solvents under reduced pressure, the residue was diluted with CH2Cl2 and the K2CO3 was removed by filtration, the organic layer was concentrated, the residue was purified by chromatography to afford 0.1 g 2-(methylamino-) naphtho[2,3-d]thiazole-4,9-dione as black solid in a yield of 0.93%. $^1$HNMR (300 MHz, DMSO) δ3.59 (s, 3H); 7.78-7.81 (m, 2H); 7.89-7.93 (m, 1H); 7.98-8.01 (m, 1H); 9.06 (br, 1H) ppm. MS-ESI: cal. 244; found: 285 (M+Na+H$_2$O).

The following compounds were prepared at the same manner as described above: 2-(4-(trifluoromethyl)phenylamino) naphtho[2,3-d]thiazole-4,9-dione: $^1$H NMR (300 MHz, DMSO) δ7.62~7.64 (dd, 2H); 7.78~7.85 (m, 5H); 7.94~7.97 (m, 1H); 9.19 (br, 1H) ppm. MS-ESI: cal. 374; found: 375 (M+1).

2-(4-(dimethylamino)phenylamino)naphtho[2,3-d]thiazole-4,9-dione: 1H NMR (300 MHz, DMSO) δ2.93 (s, 6H); 6.70~6.73 (m, 2H); 7.09~7.12 (m, 2H); 7.75~7.79 (m, 3H); 7.91~7.93 (dd, 1H); 9.02 (br, 1H) ppm. MS-ESI: cal. 349; found: 350(M+1).

2-(4-fluorophenylamino)naphtho [2,3-d]thiazole-4,9-dione: 1H NMR (300 MHz, DMSO) δ7.24~7.29 (dd, 2H); 7.39~7.44 (m, 5H); 7.75~7.83 (m, 1H); 7.93~7.95 (dd, 1H); 9.11 (br, 1H) ppm. MS-ESI: cal. 324; found: 325(M+1).

2-(pyridin-4-ylamino)naphtho[2,3-d]thiazole-4,9-dione: 1H NMR (300 MHz, DMSO) δ7.54~7.55 (m, 1H); 7.81~7.90 (m, 4H); 7.99~8.01 (dd, 1H); 8.62~8.64 (br, 2H); 9.24 (br, 1H) ppm. MS-ESI: cal. 307; found: 308(M+1).

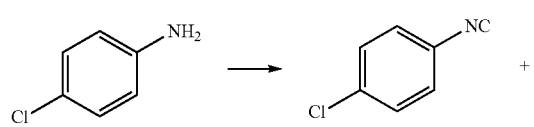

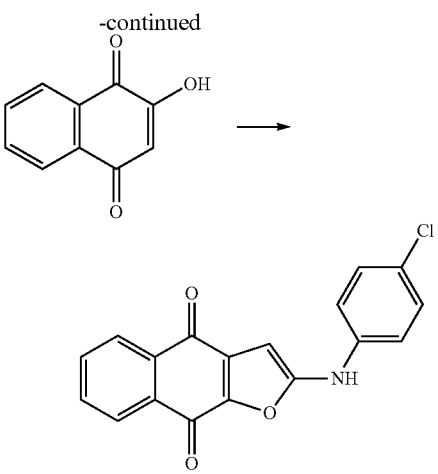

Procedure:

4-chlorobenzenamine 12.7 g (0.1 mol), and 470 mg BnEt3NCl was suspended in the mixture of 200 ml DCM, 200 ml CH$_3$Cl and 200 ml 50% KOH (aq.), then was stirred at room temperature for 2 h. The organic phase was separated, washed with water (500 ml), dried with Na2SO4 and concentrated to afford yellow oil, which was purified by chromatography; 1-chloro-4-isocyanobenzene 500 mg, 2-hydroxynaphthalene-1,4-dione 635 mg (1.0 eq) and Paraformaldehyde 109 mg (1.0 eq) was dissolved in 30 ml toluene, stirred and refluxed under N2 for 4 h. After removing all solvents under reduced pressure, the residue was purified by chromatography to afford 2-(4-chlorophenylamino)naphtho[2,3-b]furan-4,9-dione as black solid. 1H NMR (300 MHz, DMSO) δ6.39 (s, 1H); 7.24~7.29 (m, 2H); 7.41~7.43 (dd, 2H); 7.54 (br, 1H); 7.69~7.73 (t, 1H); 7.78~7.82 (t, 1H); 8.13~8.17 (t, 3H) ppm. MS-ESI: cal. 323; found: 346 (M+Na).

Plasmids

The cDNA encoding wild type IR was introduced into the pcDNA3.1/V5-His-TOPO vector. The fragments of extracellular IR, intracellular IR, extracellular IGFR, intracellular IGFR, and intracellular EGFR were amplified from wild type human IR, IGFR, or EGFR cDNA, respectively. The PCR fusion of the amplified fragments was carried out. Then the cDNA encoding extracellular IR was fused to intracellular IGFR or EGFR, and the extracellular IGFR was fused to intracellular IR and introduced into pcDNA3.1/V5-His-TOPO vector.

Cell-Based Screen

CHO-IR cells were seeded in a 96-well plate at 15,000 cells per well in 100 W of 0.1% FBS medium with 0.1% FBS. Cells were incubated overnight, followed by 15 min treatment with 10 μM compounds in DMSO (10 mM stock concentration from the Spectrum Collection Library) at 37° C. Control wells received vehicle or 100 nM insulin. Cells were lysed, and phosphorylated receptors were captured with pY20 immobilized on ELISA plates. Bound receptors were washed, then detected using an anti-IR beta antibody, followed by an horseradish peroxidase-conjugated secondary antibody and colorimetric detection with 3,3',5,5'-tetramethylbenzidine.

Immunoblotting

Cells were growth in 0.1% FBS medium overnight and then stimulated with compound or insulin, whole-cell extracts were resolved on SDS-PAGE and immunoblotted. After a 12 h fasting, C57BL/6J mice were orally administrated with 20 mg/kg of compound in 0.5% methylcellulose, and sacrificed at 3 h, 4 h and 5 h following compound administration. Fat tissues were dissected quickly and frozen on dry ice. Fat lysates were prepared and analyzed by Western blotting.

Insulin Competition Assay

The FITC-insulin (10 nM) was incubated with CHO or CHO-IR cells in the presence of various concentrations of 4524-E7 in binding buffer (F12-HAM'S, 0.5% BSA, 20 mM HEPES pH8.0, and 0.1% $NaN_3$) overnight at 4°C. Cells were washed three times, acquired on a FACScan, and the mean channel fluorescence (MCF) of bell-shaped histograms was analyzed using the CellQuest program.

IR In Vitro Kinase Assay

Recombinant GST-IRTK was incubate with 50 mM tris-HCl (pH7.4), 10 mM MgCl2, and 50 µM ATP with different concentration of compound for 15 min at 25° C. Histone H2B (0.35 µg/ml) and [γ32P]ATP (0.25 µCi/ul) were added and the samples were further incubated for 10 min. The sample was separated on a SDS-polyacrylamide gel and autoradiographed.

Partial Proteolysis 200 ng GST-IRTK was subjected to limited trypsin digestion in the presence or absence of 50 µM compound with 50 mM tris-HCL (pH8.2) and 20 mM CacCl2. The sample was separated on a SDS-polyacrylamide gel and stained by silver.

IR Dimerization Assay

HEK293 cells that were transfected with GST-IR and Myc-IR full length or Myc-IR truncations for 30 hours, were rendered quiescent by serum starvation overnight, and then stimulated with vehicle, and 5 µM 4524-E7 for 30 min, or 100 nM insulin for 15 min at 37° C. HEK293 cells that were transfected with GST-IGF-IR and Myc-IGF-IR full length were stimulated with vehicle, and 5 µM 4524-E7 for 30 min, or 100 nM IGF-1 for 15 min at 37° C. Cells were washed once in PBS, and lysed in lysis buffer (50 mM Tris, pH 7.4, 150 mM NaCl, 1 mM EDTA, 0.5% Triton X-100, 1.5 mM Na3VO4, 50 mM NaF, 10 mM sodium pyrophosphate, 10 mM sodium beta-glycerophosphate, 1× proteinase inhibitor cocktail). Transfected IR or IGF-1R receptors were pulled down with glutathione beads, and the coprecipitated proteins were resolved on SDS-PAGE. Immunoblotting analysis was performed with a variety of antibodies.

UV-Absorption Spectra

UV-Vis absorption for protein binding was obtained using the Cary 300 UV-Visible spectrophotometer (Varian Inc., Palo Alto, Calif.) equipped with 1.0 cm quartz cells. The spectra were scanned from 200 to 800 nm in Tris buffer (0.01M Tris, 0.05M NaCl, 10 mM MgCl2, pH 7.8). During the spectrophotometric titrations, protein (GST or GST-IRTK) was added to a cell containing a constant amount of compound. The absorbances at 602 nm were recorded (data were read for three times and mean value was obtain by averaging) and the obtained data were processed with KaleidaGraph (Synergy Software). Repeated measurements were done for all the samples and no significant differences were observed (The reproducibility errors is less than 5%). Binding results from the UV titration experiments were fit with a one site interaction model:

$$r=K*Cfree/(1+K*Cfree)$$

Where r represents the moles of bound compound per mole of protein, K is macroscopic binding constants, and Cfree is the free compound concentration in equilibrium with the complex.

Insulin Competition Assay

The FITC-insulin (100 nM) was incubated with CHO or CHO-IR cells in the presence of various concentrations of DDN in binding buffer (F12-HAM'S, 0.5% BSA, 20 mM HEPES pH8.0, and 0.1% NaN3) overnight at 4° C. Cells were washed three times, acquired on a FACScan, and the mean channel fluorescence (MCF) of bell-shaped histograms was analyzed using the FlowJ program.

[3H] 2-Deoxyglucose Transport

NIH 3T3-L1 preadipocytes and MEFs were grown in standard media. MEF were continuously passed in standard media to generate spontaneously immortalizedfibroblasts. After 2 d, NIH 3T3-L1 preadipocytescells were switched to differentiation media with 1 mM dexamethasone, 10 µg/ml insulin, and 0.5 mM 3-methyl-1-isobutylxanthine for 2 d, grown in post-differentiation medium containing 10 µg/ml insulin for 5 d, and then placed in standard media. 3T3-L1 adipocytes were reseeded into 12-well plates 10 to 12 days after differentiation. Cells in 12-well plates were rinsed three times with PBS at 23° C. and preincubated with 500 µl of KRP-HEPES buffer (131.2 mM NaCl, 4.71 mM KCl, 2.47 mM CaCl2, 1.24 mM MgSO4, 2.48 mM NaH2PO4, 10 mM HEPES, and 0.5% bovine serum albumin, pH 7.45) containing insulin for 15 min or compound for 30 min at 37° C. The transport reaction was initiated by adding 2-deoxyglucose (final 100 uM) with [3H] 2-deoxyglucose (0.2 µCi/well). After a 10 min incubation period, cells were washed three times with ice-cold PBS, solubilized in 1% SDS, 1M NaOH. After neutralization, radioactivity was measured by scintillation counting Fatty Acid Oxidation Assay Fatty acid oxidation was measured by determining the production of 3H2O from [9, 10-3H] palmitate. Differentiated NIH3T3-L1 were plated (0.5×105 cell per well) in a 12-well plate for 1 day. On the day of experiment, [9, 10(n)-3H] palmitatic acid (1 µCi/well), 22 µM unlabeled palmitatic acid and 0.5 mg/ml fatty acid-free BSA were added and incubated for 2 h at 37° C. After incubation, the medium was removed and extracted with Chloroform/Methanol (2:1), and the aqueous phase containing 3H2O was collected and used for radioactivity measurement in a liquid scintillation counter.

Blood Glucose Level Test

After a 12 h fasting, C57B5L/6J and db/db mice were bled from the tail vein for a baseline measurement with a glucometer (Accu-Chek; Roche Diagnostics, Indianapolis, Ind.). Afterward, animals were orally administered 5 mg/kg compound in 0.5% methylcellulose through a feeding needle. Blood glucose levels were measured at hourly intervals over 5 h.

Hyperinsulinemic-Euglycemic Clamp

C57B5L/6J mice were fasted for 12 h. One h before the clamp assay, the animals were orally administered with 5 mg/kg 4524-E7 in 0.5% methylcellulose. In vivo hepatic glucose output was then determined by hyperinsulinemic-euglycemic clamp.

Intraperitoneal Glucose Tolerance Test

After a 12 h fasting, ob/ob mice were bled from the tail vein for a baseline (time −60 minutes) measurement. Then animals were orally administered 5 mg/kg compound in 0.5% methylcellulose. One hour after the drug administration, glucose (2 g/kg) was administrated intraperitoneally. Blood glucose levels were measured 0, 30, 60, 90, 120, and 180 min after administration of glucose. The blood was collected in tubes, kept at 4° C. overnight, and plasma was prepared by centrifugation (2,000 g, 20 min). Plasma insulin was measured by enzyme-linked immunosorbent assay with a rat insulin kit (Crystal Chem. Inc., USA). Insulin was quantified using the insulin standard curve.

Example 1

DDN and CSN Activate IR and Insulin-Mediated Signaling Cascades

Figure 1:
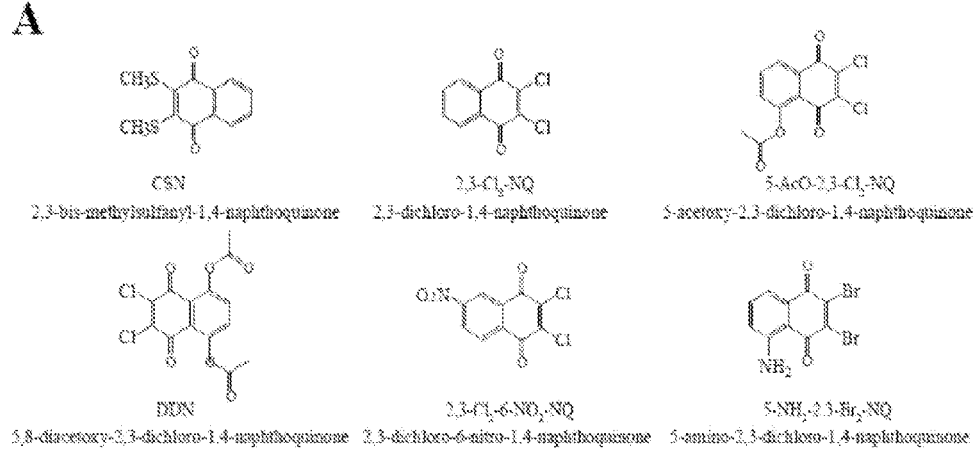
FIG. 1 illustrates the chemical structure of insulin mimetics. (A) Chemical structures of six compounds of 1,4-Naphthoquinone derivatives. (B) Effects 1,4-Naphthoquinone derivatives on IR Phosphorylation in CHO-IR cells. CHO-IR cells were treated with different 1,4-naphthoquinone derivatives (5 µM) or insulin (100 nM) for 15 mins. The amount of phosphorylated IR receptors was quantified by sandwich ELISA using immobilized anti-phosphotyrosine antibodies (pY20) anti-IR antibody. The activities of tested compounds were expressed as a percentage of the vehicle (DMSO) (n=3).
Figure 1:
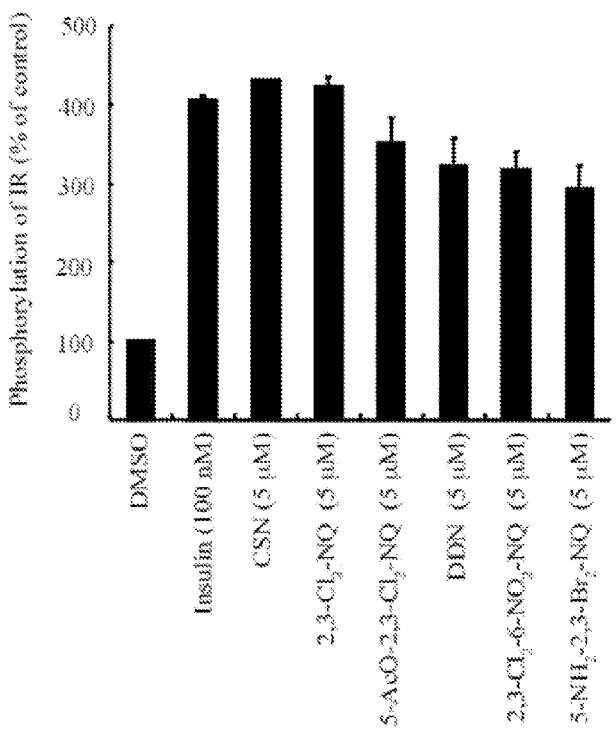
Figures 1, 2:
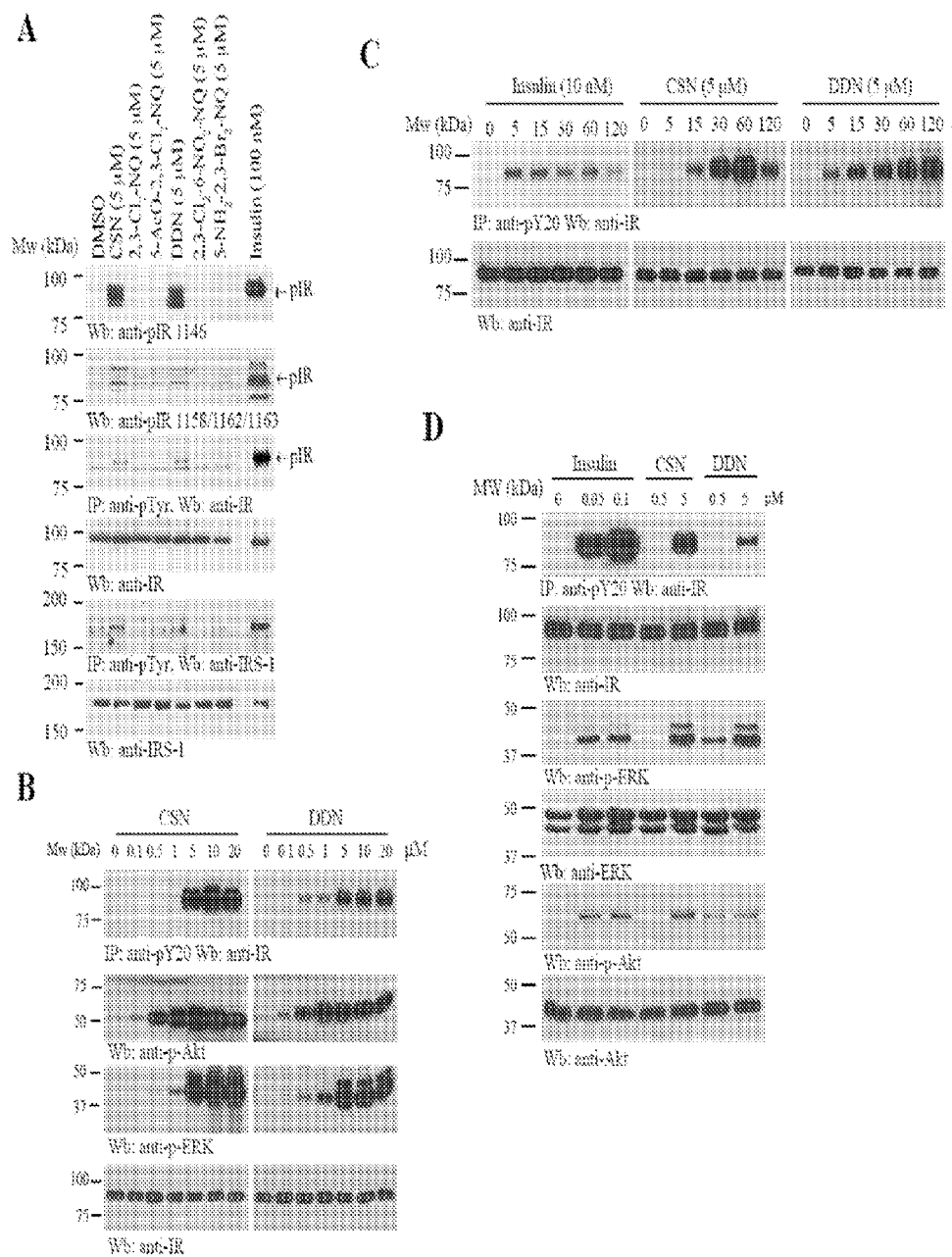
FIG. 2 shows data suggesting DDN and CSN activate IR and its downstream signaling.
Figure 2:
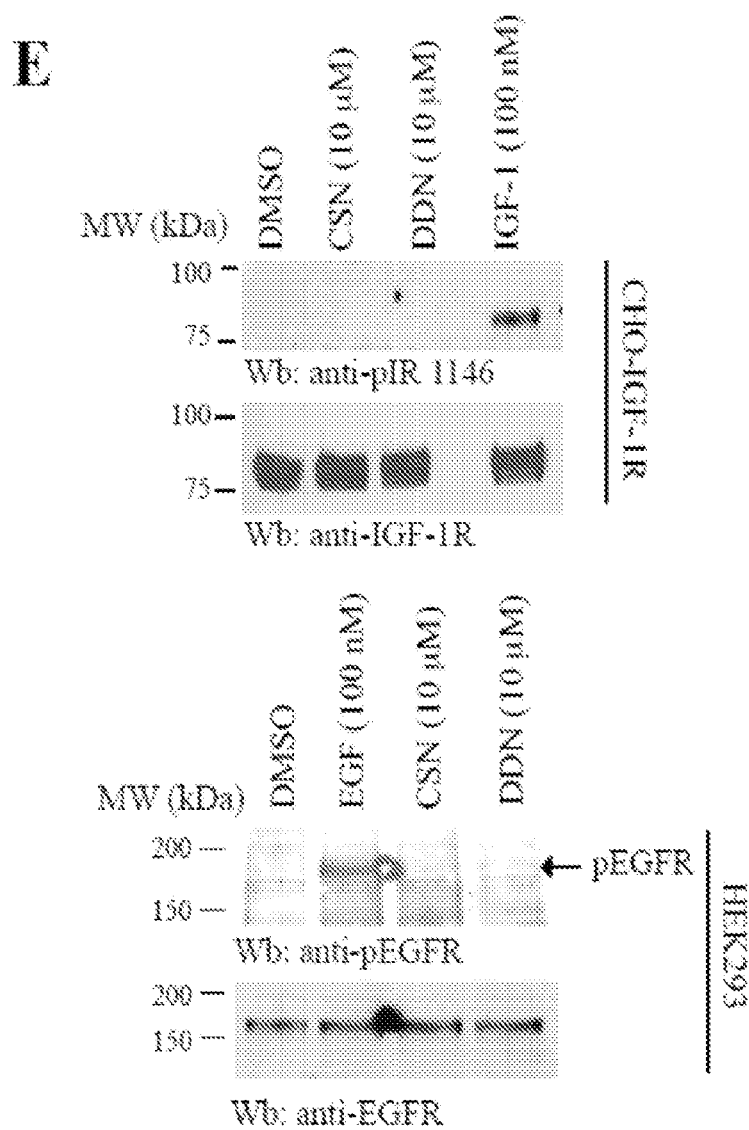

A cell-based ELISA assay was developed with an IR stably transfected Chinese Hamster Ovary (CHO-IR) cell line. The cells were seeded in a 96-well plate and treated with 10 µM (15 min) compounds. The cell lysates were subjected to the sandwich ELISA using immobilized anti-phosphotyrosine antibody and anti-IR antibody. The positive hits were subsequently analyzed on CHO-IGF-1R cells and the compounds that failed to activate IGF-1R were chosen. Among the positive hits, 1,4-naphthoquinone compounds were identified that can selectively activate IR but not IGF-1R (FIG. 1A). ELISA results revealed that all these compounds can significantly induce IR phosphorylation (FIG. 1B). Surprisingly, immunoblotting analysis demonstrated that only 2,3-bis-methylsulfanyl-1,4-naphthoquinone (CSN) and 5,8-diacetoxy-2,3-dichloro-1,4-naphthoquinone (DDN) strongly stimulated tyrosine phosphorylation of the IR β subunit in Y1146 (FIG. 2A, 1st panel) and Y1158/1162/1163 (FIG. 2A, 2nd panel). Total IR tyrosine phosphorylation was further confirmed by immunoprecipitation using anti-phosphotyrosine (PY20) antibody (FIG. 2A, 3rd panel). Presumably, the discrepant IR phosphorylation levels between ELISA and immunoblotting assay was caused by nonspecific signal and low detection limit of the ELISA. Consistent with IR activation, the tyrosine phosphorylation of IRS-1 of CHO-IR cells was also increased when stimulated by both DDN and CSN (FIG. 2A, 5th panel). Titration assay showed both compounds activated IR in a dose dependent manner. At 5 µM, both compounds evidently stimulated IR phosphorylation and downstream Akt and ERK activation in a dosedependent manner (FIG. 2B). The time course assay demonstrated that these CSN activated IR in CHO-IR cells at 5-15 min, peaked at 60 min, and the signal decreased at 2 h (FIG. 2C, middle panel). In contrast, significant IR phosphorylation started 5 min after DDN stimulation, and the signals escalated with the time course (FIG. 2C, right panel). While insulin activated IR signaling at 0.05 µM, these compounds stimulated the IR signal cascades at 5 µM (FIG. 2D). Neither IGF-1R nor EGFR was activated by these compounds even at 10 µM, underscoring that these molecules possess selectivity towards different receptors (FIG. 2E). Hence, both DDN and CSN potently and specifically stimulate IR and its downstream signaling cascades in intact cells.

Example 2

DDN Displays Hypoglycemic Effect in Mice

To explore whether DDN and CSN can mimic insulin in provoking IR and its downstream IRS-1 activation in vivo, various doses of DDN and CSN were intraperitoneally administrated into C57BL/6J mice. However, CSN was lethal to the mice even at low doses (1 mg/kg) (data not shown). Whether DDN possesses hypoglycemic functions were tested. After oral injection, DDN significantly reduced blood glucose in C57BL/6 mice as compared to vehicle control. The kinetics of DDN in lowering blood glucose is different from that of insulin. Thirty min after i.p injection of insulin, the blood glucose concentration was reduced; however significant decrease of blood glucose could only be detected after 3 h of DDN administration. On the other hand, injection of the inactive analogue 2-amino-1,4-naphthoquinone (2NH2-NQ) at the same dosage had no effect (FIG. 3A for the percentage change and Fig S1 for the absolute blood glucose concentrations).

To monitor the IR signaling cascades in insulin sensitive tissues, 20 mg/kg DDN was injected into C57BL/6J mice via oral gavage, and sacrificed the animals at different time points and monitored IR tyrosine phosphorylation by immunoblotting. In liver and muscle, DDN elicited demonstrable IR activation after 3-4 h (FIG. 3B, 1st panel). Immunoprecipitation using PY20 antibody also confirmed IRS-1 tyrosine phosphorylation in both tissues after stimulated by DDN (FIG. 3B, 3rd panel); in contrast, DDN did not stimulate IGF-IR activation in either muscle or liver (FIG. 3B, 5th panel), which concurred with in vitro observation (FIG. 2E). Neither IR nor IRS phosphorylations were increased after 2NH2-NQ injection (FIG. 3B). To test whether DDN has an acute effect as insulin, DDN or 2NH2-NQ was injected into the animal via vena cava. The liver was then dissected and homogenized after 5 min. Immunoprecipitation using PY20 antibody demonstrated that DDN, but not 2NH2-NQ, quickly activated IR (FIG. 3C, 1st panel), Akt and ERK (FIG. 3C, 3rd and 5th panels). Similarly to the observation in C57/BL6 mice, DDN induces IR signaling in the well-established mice models of non-insulin-dependent diabetes mellitus. Oral injection of DDN enhanced IR and ERK phosphorylations in db/db (FIG. 4A) and ob/ob mice (FIG. 4B). One h after oral administration of DDN, lower blood glucose was found in db/db mice as compared to vehicle control (FIG. 4C). In contrast to the findings in C57/BL6 mice, the time needed for DDN to lower the blood glucose in db/db mice is comparable to that of insulin injection, but the effect of DDN can sustain till the end of the experiment whereas the effect of insulin vanished 2 h after injection. Oral administration of DDN to ob/ob mice also led to significant improvement in glucose tolerance, which is comparable to the effect of insulin injection (FIG. 4D). Nonetheless, single oral doses of DDN had no significant effect on plasma insulin levels in ob/ob mice (data not shown), suggesting the hypoglycemic function of DDN is not acting through the change of insulin secretion. Treatment of wild-type C57BL/6J mice (n=5) with daily oral administration of DDN (5 mg/kg) for 16 days did not affect the food intake, or blood biochemistry. Pathological examination also failed to detect any demonstrable toxicity in brain, heart, liver, kidney and muscle, indicating that the compound might not possess any intolerable toxicity. Hence, DDN mimics insulin and effectively lowers blood glucose in wild-type and insulin-resistant db/db and ob/ob mice.

Example 3

DDN Induces Cellular Glucose Uptake

The observation that DDN effectively reduces circulating glucose in animals suggested that it might enhance glucose absorption. Therefore, the effect of DDN on glucose uptake was examined in adipocytes, a well-characterized cellular model for insulin-induced glucose homeostasis. Differentiated 3T3-L1 adipocytes were treated with various concentrations of DDN and the activation of Akt was monitored. DDN elicited a dose-dependent IR and Akt activation (FIG. 5A). Moreover, DDN escalated 3H-deoxyglucose uptake in a dose-dependent manner (FIG. 5B), which concurs with the Akt phosphorylation pattern.

DDN sensitized insulin's activity. In differentiated 3T3-L1 cells, 5 nM of insulin was able to trigger IR phosphorylation (FIG. 5C, 1st panel, lane 2). However, DDN at the same concentration did not induce any IR activation (FIG. 5C, 1st panel, lane 3). When the two insulin and DDN were added together, IR phosphorylation was higher than those observed when insulin or DDN was administrated separately, suggesting DDN can potentiate insulin's activity. Akt phosphorylation tightly correlated with the IR activity after insulin or DDN stimulation (FIG. 5C, 3rd panel). In addition, DDN elevated insulin's activity in triggering glucose uptake in differentiated 3T3-L1 cells. Consistent with the IR activation pattern, stimulation with 5 nM insulin, but not DDN significantly increased the 3H-deoxyglucose uptake in 3T3-L1 cells. When insulin and DDN were administrated together, the magnitude of glucose uptake was further increased (FIG. 5D).

To confirm that the DDN-induced biological effect is IR-dependent, IR was knocked down in the differentiated adipocytes using siRNA and monitored the insulin signaling. Western blot analysis showed that IR expression was significantly decreased in cells transfected with siRNA against IR (FIG. 5E, 1st panel). Both insulin and DDN-triggered ERK phosphorylation were reduced when IR was depleted, underscoring that IR is the molecular target of DDN to trigger ERK activation (FIG. 5E, 2nd panel). PI3K p85 subunit ablated (p85α−/−) MEF was also treated with DDN and glucose uptake activity was determined. It has been reported that MEF with p85 ablation are defective in insulin-stimulated glucose uptake. Both insulin and DDN triggered robust 3H-deoxyglucose uptake in wild-type MEF cells but not p85α−/− cells (FIG. 5F), suggesting that an intact IR/PI3K/Akt cascade is involved for DDN to exert its hypoglycemic function.

Example 4

DDN Binds to the Kinase Domain of Insulin Receptor

The synergistic function of DDN on insulin induced IR activation suggests that insulin and DDN might share differential IR binding sites. An insulin competition assay was performed using flow cytometry. CHO-IR cells were incubated with 100 nM FITC-insulin in the presence of DDN at different concentrations. The binding of FITC-insulin to the cell surface IR increased the fluorescent signal of CHO-IR cells, leading to a right shift of the peak. No significant change of the shifted peak position was observed in the presence of DDN (FIG. 6A, top panel). However, a left shift of the fluorescent peak was detected, when 5 μM unlabelled insulin was added, suggesting a successful competition between unlabelled insulin and FITC-insulin for the ligand binding (FIG. 6A, middle panel). As a negative control, FITC-insulin did not bind to the IR deficient parental CHO cells (FIG. 6A, bottom panel). These results suggest that DDN and insulin might possess different ligand binding sites on IR.

Several small molecules bind to the intracellular kinase domain of IR (IRTK) and provoke its activation. DDN might also interact with the IRTK to activate IR. To test this possibility, an UV-absorption spectra analysis was performed using recombinant IRTK. While the GST-tagged IRTK (GST-IRTK, a.a. 1011-1382) had no absorption from 200 nm to 800 nm, addition of DDN, but not its structural related analogue naptho[2,3-d]thiazole-4,9-dione-2-[(4-chlorophenyl)amino] (4524), enhanced the peak absorption at 560 and 602 nm (FIG. 6B), suggesting a specific interaction occurs between DDN and IRTK. Titration assay revealed that the binding constant Kd by DDN to GST-IRTK was approximately 3.27±1.06 μM. Partial proteolysis analysis was also performed to confirm the DDN/IRTK interaction. Recombinant GST-tagged IRTK was incubated with either DMSO or DDN, followed by limited trypsin digestions. In DMSO treatment, GST-IRTK was digested into several smaller fragments of various molecular weights. However, DDN pretreatment protected IRTK against trypsin digestion with more intact IRTK were observed (FIG. 6C). As a positive control, the presence of ATP-γ-S also altered the proteolysis pattern. Whereas a band of ~37 kDa presented strongly in the ATP-γ-S incubated IRTK, a band of ~30 kDa was found in the control samples but attenuated in the ATP-γ-S-treated sample.

Whether DDN alters the kinase activity of IRTK through direct interaction, was evaluated by performing the in vitro histone phosphorylation assay. DDN, but not the inactive analogue 2-NH2-NQ, activated the recombinant IRTK to phosphorylate histone H2B (FIG. 6D). Therefore, DDN activates IR by increasing the kinase activity of IR through direct interaction.

Example 5

4524-E7 is a Specific IR Activator

IR autophosphorylation is the hallmark of receptor activation, which in turns activates IRS-1/PI3K/Akt cascade. In agreement with the ELISA results, immunoblotting analysis revealed that 4524-E7 as well as the other 1,4-nathoquinone derivatives increased the tyrosine phosphorylation on the IR in CHO-IR cells (FIG. 7C, 1st panel). This receptor phosphorylation induced by 4524-E7 was further confirmed when anti-IR antibody was used in the immunoprecipitation. The downstream Akt activation tightly correlated with the IR phosphorylation as activated by the molecules (FIG. 7C, 3rd panel). The discrepant IR phosphorylation levels between ELISA and immunoblotting assay was probably caused by nonspecific signal and low detection limit of the ELISA. Whether 4524-E7 can activate other receptors of RTK family was tested. IR, IGF-1R, TrkB, or EGFR-transfected HEK293 cells were treated with 4524-E7 (5 μM) for 15 min. IR but not any other RTKs was selectively activated by insulin or 4524-E7, and IGF-1R, TrkB, or EGFR were specifically activated by their cognate ligands but not vehicle control or the compound (FIG. 7D). Therefore, 4524-E7 is a selective IR activator. To further explore the specificity, several hybrid recombinant RTKs were generated by replacing IGFR and EGFR's extracellular domain (ECD) with IR's ECD. Moreover, IGFR's intracellular domain (ICD) was substituted with IR's ICD, and the His-tagged receptors were transfected into CHO cells and treated with 4524-E7 for 30 min. Immunoblotting analysis of the Ni2+ column pull-down proteins revealed the selective tyrosine phosphorylation, when IR ICD was present in wild-type IR and IGFR-IR hybrid.

IR-IGFR and IR-EGFR that contain IR ECD were not phosphorylated. Consistently, Akt activation pattern tightly coupled with IR-ICD containing receptors (FIG. 7E), indicating that 4524-E7 specifically targets IR-ICD and provokes its activation. Additionally, an RTK kinase profile screen assay was conducted and it was found that none of the tested RTKs [epidemical growth factor receptors (EGFR, ErbB2), ephrin receptor (EphA1), fibroblast growth factor receptor (FGFR1), vascular endothelial growth factor receptor (VEGFR1), hepatocyte growth factor receptor (cMet), BDNF receptor (TrkB), platelet-derived growth factor receptor (PDGFRa) and glial cell line-derived neurotrophic factor receptor (RET)] were activated by this compound. Interestingly, this compound slightly inhibited FGFR1 and MET receptors at 10 μM. Taken together, our data demonstrate that 4524-E7 is a specific IR activator.

Example 6

Signaling Cascades Activated by 4524-E7

The dose-response relationship of 4524-E7 on IR activation in CHO-IR cells was studied. ELISA and western blot analysis showed that this compound activated IR in a dose-dependent manner. It started to activate IR at 2.5 μM and peaked at 10 μM (FIG. 8A, 1st panel). The immunoblotting validation using IR phosphorylation-specific antibody (Tyr1162) fitted with the quantitative results (FIG. 8A, 2nd panel). Kinetics assay demonstrated that insulin triggered IR activation at 5 min and peaked at 15 min, and the signal decayed at 30 min. By contrast, 4524-E7 stimulated IR activation at 5 min and the signal increased at 15 min and climaxed at 30 min. The signal sustained till 60 min and partially decreased at 120 min (FIG. 8B, 1st panel). Similar results were obtained in the immunoblotting analysis of IR tyrosine phosphorylation and Akt activation (FIG. 8B, 2nd and 4th panels). Biochemical analysis of the downstream Akt and Erk1/2 activation in CHO-IR cells showed that 4524-E7 significantly elevated Akt phosphorylation with a concentration as low as 0.5 μM (FIG. 2C, top panel). Akt phosphorylation escalated as the concentration increased. On the other hand, Erk1/2 activation was detected, when 5 μM higher concentration of 4524-E7 was used (FIG. 8C, 3rd panel). Insulin stimulated both Akt and Erk1/2 activation at 0.01 μM and it further upregulated these downstream effectors at 0.05 μM (FIG. 8C).

Example 7

4524-E7 Promotes Glucose Uptake in Adipocytes

To determine whether 4524-E7 could activate endogenous IR and sensitize insulin's action on IR-mediated signaling cascades, differentiated 3T3-L1 adipocytes were treated with different concentrations of 4524-E7 in the presence or absence of 10 nM insulin. Immunoblotting analysis showed that this small molecule could activate the endogenous IR (FIG. 9A, 1st panel, lanes 1, 3, 4 and 5). Akt and Erk1/2 phosphorylation tightly correlated with the IR activation status (FIG. 9A, 7th and 9th panels, lanes 1, 3, 4 and 5). A mixture of insulin and 4524-E7 provoked much more robust IR, Akt and Erk1/2 phosphorylation than insulin or 4524-E7 alone, indicating an additive effect by 4524-E7 on insulin-mediated IR activation (FIG. 9A, 1st, 7th and 9 panels, lanes 6 to 8). Quantification of the phosphorylation signal versus the total protein level suggested a synergistic effect. The stimulatory activity by 4524-E7 on IR signaling cascades was specific, as neither IGF-1R nor EGFR was activated by this compound (FIG. 9A, 3rd and 5th panels). Moreover, no additive effect was observed for 4524-E7 on EGFR or IGFR activation by EGF or IGF-I, respectively.

In muscle and white adipose tissues (WAT), insulin acts as an essential hormone to promote glucose uptake. To examine whether 4524-E7 mimics insulin in triggering glucose uptake, an in vitro glucose uptake assay was performed in the differentiated 3T3-L1 adipocytes. The differentiated 3T3-L1 adipocytes were treated with various concentrations of 4524-E7 and the amount of [3H]-2-deoxyglucose taken by the cells was measured. As shown in FIG. 9B, 4524-E7 stimulated glucose uptake in a dose-dependent manner (FIG. 9B, lanes 4 to 6). 4524-E7-induced glucose uptake was significantly elevated in a concentration as low as 1 μM. At 5 μM, 4524-E7 nearly quadrupled the glucose uptake as compared to control. In agreement with the IR phosphorylation status, the glucose uptake was additively escalated when a mixture of 10 nM insulin and 4524-E7 was used versus these two agents alone (FIG. 9B, lanes 7 to 9). These results suggest that 4524-E7 has a potent additive effect with insulin to induce glucose uptake. In addition to the increased glucose uptake, insulin is recognized as an anti-lipogenic factor in adipocytes. To test if 4524-E7 also inhibits lipolysis, an in vitro lipid oxidation assays were performed. In differentiated 3T3-L1 adipocytes, insulin stimulation decreased lipid oxidation to ~70% of the control (FIG. 9C). Similarly, 4524-E7 challenge reduced lipid oxidation to ~50% of the DMSO-treated treated cells. Therefore, 4524-E7 not only resembles insulin in enhancing glucose uptake but also inhibiting lipid oxidation in adipocytes.

To confirm whether 4524-E7 exerts its biological functions is IR-dependent, using siRNA IR was knocked down in the differentiated adipocytes and the insulin signaling after 4524-E7 treatment was monitored. Western blot analysis showed that IR expression was significantly decreased after si-RNA transfection. Both insulin and 4524-E7-triggered Akt and ERK phosphorylation were also reduced, when IR was depleted, underscoring that IR is the major molecular target of 4524-E7 to trigger Akt activation (FIG. 9D). Depletion of IR substantially diminished glucose uptake by insulin or 4524-E7. PI3K p85 subunit ablated (p85α-/-) MEF cells were also treated with 4524-E7 and determined its glucose uptake activity. It has been reported that p85α-/- MEFs are defective in insulin-stimulated glucose uptake, although p85α knockout mice are hypoglycemic. As expected, both insulin and 4524-E7 triggered robust [3H]-2-deoxyglucose uptake in wild-type MEF cells. However, neither insulin nor 4524-E7 was able to induce glucose uptake in p85α-/- cells (FIG. 9E). Therefore, 4524-E7 mimics insulin's functions by activating IR and PI3K signaling.

Example 8

4524-E7 Interacts with Insulin Receptor Tyrosine Kinase Domain

In vitro data shows that 4524-E7 has an additive effect with insulin on IR activation (FIGS. 9A and B), suggesting that these two agents might have different receptor binding sites. Whether 4524-E7 competes with insulin for binding IR using flow cytometry assay was tested. CHO-IR cells were incubated with 10 nM FITC-insulin in the presence of different concentrations of 4524-E7. While binding of FITC-insulin to the cell surface IR increased the fluorescent signal of CHO-IR cells, leading to a right shift of the peak, no significant change of the shifted peak position was observed in the presence of 4524-E7 (FIG. 10A, left panel). However, a left shift of the fluorescent peak was detected, when 1 μM unlabelled insulin was added, suggesting a successful competition between unlabelled insulin and FITC-insulin for the ligand binding (FIG. 10A, middle panel). As a negative control, FITC-insulin did not bind to the parental CHO cells (FIG. 10A, right panel). These results suggest that 4524-E7 and insulin might have differential ligand binding sites on IR.

To evaluate if 4524-E7 directly binds to the IR kinase domain, a partial proteolysis assay was performed with recombinant IRTK domain using trypsin or chymotrypsin, which was used before to characterize the interaction between IR and its small molecular ligand DAQ B1. Recombinant GST-tagged IRTK with either DMSO, 50 μM 4524-E7 or ATP-γ-S, were incubated and followed by limited trypsin or chymotrypsin digestion. Under DMSO treatment, GST-IRTK was quickly digested by both trypsin and chymotrypsin into several small fragments with various molecular weights (FIG. 10B). However, the digestion pattern was altered in the presence of 4524-E7. Specifically, more intact IRTK was observed in 4524-E7-treated samples. Interestingly, the fragments of ~25 and ~40 kDa were diminished in trypsin-treated IRTK in the presence of 4534-E7, although the ~30 kDa segment was slightly increased when compared to the DMSO-treated sample (FIG. 10B). As a positive control, the digestion pattern was altered, when IRTK was pre-incubated with ATP-γ-S. These data suggest that 4524-E7 directly interacts with IRTK, leading to a change of the protein conformation and protection of the IRTK from proteolysis. To test whether 4524-E7 selectively elevates IR kinase activities, an in vitro IR, IGFR, and EGFR kinase assays were performed using histone as the substrate. Histone phosphorylation by recombinant IR tyrosine kinase was greatly enhanced by 4524-E7 in a dose-dependent manner (FIG. 10C), while 4524-E7 has no effect on histone phosphorylation by recombinant IGFR or EGFR tyrosine kinase, which implies that 4524-E7 specifically interacts and activates the kinase activity of IR.

IRTK shares ~84% structural identity with the kinase domain of IGF-1R, yet 4524-E7 can distinguish the two kinases unambiguously, suggesting that the compound interacts with a unique structure of IRTK to enhance its activity. two potential binding regions were identified between the nucleotide binding site and the catalytic loop of IRTK using the amino acid alignment between the human IR and IGR-1R. To test if these regions are the action sites of 4524-E7, several GFP-tagged hybrid kinases were generated with R1 (GFP-IRTK R1), R2 (GFP-IRTK R2) or both (GFP-IRTK R1+R2) regions of IRTK and replaced with the corresponding sequence of IGF-1R. These mutants were then used to perform the in vitro kinase assay in the presence of 4524-E7. As shown in FIG. 10E, replacing the R2 region of IRTK with IGF-1R abolishes the kinase stimulatory effect by 4524-E7. Thus, 4524-E7 might bind to the motif (1117 to 1125 a.a.) of IRTK to stimulate the kinase activity, which provides an explanation for its preference towards the IR versus IGF-1R.

Example 9

4524-E7 Exhibits Hypoglycemic Effect in Diabetic Mouse Models

4524-E7 activates IR in vivo. Fasted C57BL/6J mice were administrated orally with vehicle or 4524-E7 and IR phosphorylation in liver, muscle, and WAT was analyzed at different time intervals. Fitting with the in vitro results, IR tyrosine phosphorylation in the liver, muscle and WAT were all elevated 3 h after 4524-E7 administration (FIG. 11A). Pretreatment of 4524-E7 to the animals potentiated the insulin actions in suppressing hepatic glucose output during the hyperinsulinemic-euglycemic clamp assay (FIG. 11B), which concurred with our results shown in FIGS. 9A and B. Blood glucose level was also decreased in fasted animals treated with 4524-E7. Circulating blood glucose in wild-type C57/BL6 mice was significantly decreased to 70% of basal level 3~4 h after a single oral administration of 4524-E7 (FIG. 11C). A more potent glucose correction effect was detected in db/db mice. One hour after oral administration of 4524-E7, blood glucose in the tested db/db mice was decreased to about 50% of the initial value (FIG. 11D), suggesting the blood glucose lowering function of 4524-E7 might be more efficacious in hyperglycemic model. Moreover, oral administration of 4524-E7 resulted in a significant improvement of glucose tolerance in ob/ob mice, which further suggests that 4524-E7 is an effective agents in controlling blood glucose even in the tissues that are insulin resistant (FIG. 11E).

Example 10

Structure-Activity Relationship (SAR) Studies on the IR Activating Properties of 4524-E7

A panel of analogues were synthesized and tested their agonistic effect (FIG. 12A). CHO-IR cells were treated with 5 µM of the compounds for 30 min and monitored the IR phosphorylation using ELISA. Notably, addition of a chloro-group on 2' position (compound 7) elicited improved activity to the parental compound the IR stimulatory activity of these compounds were examined using immunoblotting assay. In alignment with the ELISA assay, both 4524-E7 and compound 7 triggered IR tyrosine phosphorylation (FIG. 12C).

The invention claimed is:
1. A method of treating diabetes, insulin resistance, or hyperglycemia comprising administering to a subject diagnosed with, or exhibiting symptoms of diabetes, insulin resistance, or hyperglycemia a pharmaceutical composition comprising a compound of formula I

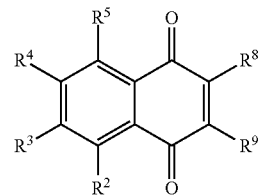

formula I or pharmaceutically acceptable salts thereof wherein, $R^2$ and $R^5$ are not hydroxy or alkoxy;
$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^6$;
$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^6$;
$R^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^6$;
$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;
$R^6$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$;

$R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl,N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^8$ and $R^9$ are halogen;

$R^{10}$ alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$ $R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. A method of treating diabetes, insulin resistance, or hyperglycemia comprising administering to a subject diagnosed with, or exhibiting symptoms of diabetes, insulin resistance, or hyperglycemia a pharmaceutical composition comprising a compound of formula IA,

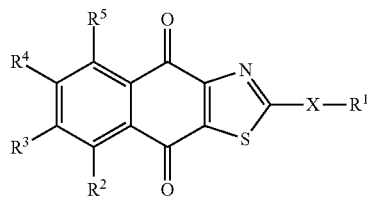

formula IA or pharmaceutically acceptable salts thereof wherein,

X is NH, O, or S;

$R^1$ is alkyl, formyl, carboxy, carbamoyl, carbocyclyl, aryl, or heterocyclyl, wherein $R^1$ is optionally substituted with one or more, the same or different, $R^6$;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^6$;

$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^6$;

$R^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^6$;

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl,N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

3. The method of claim 2, wherein X is NH.

4. The method of claim 2, wherein $R^1$ is carbocyclyl, aryl, or heterocyclyl optionally substituted $R^6$.

5. The method of claim 2, wherein $R^6$ is a halogen.

6. The method of claim 2, wherein $R^2$ and $R^5$ are not unsubstituted hydroxy.

7. The method of claim 2, wherein $R^2$ and $R^5$ are hydrogen.

8. The method of claim 2, wherein the subject is diagnosed with Type 1 or Type 2 diabetes.

9. The method of claim 2, wherein the compound is selected from 2-((4-chlorophenyl)amino)naphtho[2,3-d]thiazole-4,9-dione, and 2-((2,4-dichlorophenyl)amino)naphtho [2,3-d]thiazole-4,9-dione.

10. The method of claim 1, wherein $R^2$ and $R^5$ are hydroxy substituted with formyl, wherein formyl is substituted with $R^7$.

11. The method of claim 1, wherein the compound selected from:

5,8-diacetyloxy-2,3- dichloro-1,4-naphthoquinone and
5-acetyloxy-2,3- dichloro-1,4-naphthoquinone.

* * * * *